(12) United States Patent
Lu et al.

(10) Patent No.: US 12,371,405 B1
(45) Date of Patent: Jul. 29, 2025

(54) ISOINDOL-SULFILIMINE COMPOUND AND USE AS A SIGMA-2 RECEPTOR INHIBITOR THEREOF

(71) Applicant: SHANGHAI UNIVERSITY OF MEDICINE AND HEALTH SCIENCES, Shanghai (CN)

(72) Inventors: Xiuhong Lu, Shanghai (CN); Gang Huang, Shanghai (CN); Anyang Sun, Shanghai (CN); Yongsheng Zhang, Shanghai (CN); Jincheng Wang, Shanghai (CN); Jinjing He, Shanghai (CN)

(73) Assignee: SHANGHAI UNIVERSITY OF MEDICINE AND HEALTH SCIENCES, Shanghai (CN)

( * ) Notice: Subject to any disclaimer, the term of this patent is extended or adjusted under 35 U.S.C. 154(b) by 0 days.

(21) Appl. No.: 19/058,309

(22) Filed: Feb. 20, 2025

Related U.S. Application Data

(63) Continuation of application No. PCT/CN2024/106052, filed on Jul. 17, 2024.

(30) Foreign Application Priority Data

Jan. 24, 2024 (CN) .......................... 202410096801.6

(51) Int. Cl.
*C07D 209/44* (2006.01)

(52) U.S. Cl.
CPC ................................ *C07D 209/44* (2013.01)

(58) Field of Classification Search
CPC .................................................... C07D 209/44
See application file for complete search history.

(56) References Cited

FOREIGN PATENT DOCUMENTS

| CN | 106163516 B | 11/2016 |
|---|---|---|
| CN | 115397849 A | 11/2022 |
| CN | 116867488 A | 10/2023 |
| CN | 117945980 A | 4/2024 |
| WO | 2019089988 A1 | 5/2019 |

*Primary Examiner* — Shawquia Jackson
(74) *Attorney, Agent, or Firm* — JEEN IP LAW, LLC

(57) ABSTRACT

The present invention relates to an isoindol-sulfilimine compound and its preparation and its use as a sigma-2 receptor inhibitor. Compared with the prior art, the isoindol-sulfilimine compound prepared by the present invention can effectively inhibit the sigma-2 receptor activity by binding to the sigma-2 receptor and deformationally regulating the sigma-2 receptor complex, which will lead to the instability of the binding of adjacent Aβ oligomers to the receptor on the synapse, thus leading to the removal of AB oligomers from the synapse. It can be further used for the preparation of new therapeutic drugs for tumor and neurodegenerative diseases.

2 Claims, No Drawings

ISOINDOL-SULFILIMINE COMPOUND AND USE AS A SIGMA-2 RECEPTOR INHIBITOR THEREOF

CROSS-REFERENCE TO RELATED APPLICATIONS

This application is a continuation of PCT/CN2024/106052, filed on 17 Jul. 2024 and claims priorities to Chinese Patent Application No. 202410096801.6, filed on Jan. 24, 2024, the contents of which are hereby incorporated by reference.

TECHNICAL FIELD

The present invention relates to the technical field of pharmaceutical chemistry and, in particular, to an isoindol-sulfilimine compound and its preparation and use as a sigma-2 receptor inhibitor thereof.

BACKGROUND

Alzheimer's disease (AD) is a group of neurodegenerative disorders, its main clinical manifestations are progressive loss of language, memory and cognitive functions. The treatment of AD has been challenging over the past decades; on the one hand, the cost of treatment and care for AD worldwide is enormous. On the other hand, with the exception of aducanumab and Lecanemab (*Brain.* 2023, 146 (10), 3969-3990), the Food and Drug Administration (FDA) has not approved a single drug for the treatment of AD since 2003. The main drugs currently used clinically for the treatment of AD are donepezil, carboplatin, galantamine, and memantine. Donepezil, carboplatin and galantamine are acetylcholinesterase inhibitors (AChEI). Memantine is an N-methyl-D-aspartate (NMDA) receptor antagonist. However, these drugs only temporarily slow down the disease process and do not completely treat AD. According to the International AD Association, it is estimated that about 50 million people suffered from dementia in 2018 and it is expected to triple by 2050 (*Alzheimers Dement.* 2023, 19 (4), 1598-1695). Therefore, the development of drugs for treating AD is a daunting task, and research and development of drugs for treating AD is imminent due to high healthcare costs and the increasing number of people suffering from the disease.

Sigma-2 receptors are a class of receptors widely distributed in peripheral tissues such as the central nervous system, pancreas, liver, and gastrointestinal tract, which may be potential targets for the treatment of tumors, neurodegenerative diseases, and neuropathic pain. In recent years, sigma-2 receptors have been isolated from calf liver (*Proc. Natl. Acad. Sci. U.S.A* 2017, 114 (27), 7160-7165), and by means of biochemical analysis the sigma-2 receptor was considered to be transmembrane protein 97 (TMEM97). TMEM97 associates with the low-density lipoprotein receptor (LDLR), and the use of siRNA knockdown of TMEM97 decreases the endocytosis of low-density lipoprotein (LDL) by the LDLR. Other studies have found that sigma-2/TMEM97 receptor and PGRMCI are jointly involved in the process of LDL-LDLR complex formation and are important for LDL uptake. In addition, activation of the sigma-2/TMEM97 receptor is neuroprotective (*ACS Chem Neurosci,* 2019, 10 (3), 1595-1602). 2021, the crystal structure of the sigma-2 receptor has also been resolved, which provides a great convenience for the design of sigma-2 receptor ligands (*Nature* 2021, 600 (23), 759).

A synapse is a structure in which impulses from one neuron are transmitted to another neuron or to another intercellular contact, and it is the site where functional connections between neurons occur. It has been shown that some populations do not develop AD even when their brains have AD-related pathologic features (e.g., amyloid plaques and neurofibrillary tangles), possibly because the unique synaptic protein composition of such populations is resistant to β-amyloid and tau proteins, thus avoiding their impairment of synaptic function. For most AD patients, however, Aβ oligomers cause synaptic dysfunction and synapse loss by binding to a variety of receptors on the synapse, which in turn affects the transmission of information between neurons in the brain. Cognition Therapeutic has found that inhibition of the sigma-2 receptor destabilizes the binding of Aβ oligomers to synaptic receptors, resulting in the removal of Aβ oligomers from synapses and the restoration of synaptic function. Cognition Therapeutic utilized supercritical fluid extraction (SFE) to discover that N-arylpropyl-N-arylmethylamine or arylpropylisoindole compounds from ginger oil have good sigma-2 receptor binding activity, and after docking and designing the crystal structure of the sigma-2 receptor protein, we obtained a candidate compound, CT1812, which has good ex vivo and in vivo activity and the ability to cross the BBB, The in vivo probe test has demonstrated that CT1812 can increase the concentration of cerebrospinal fluid β-amyloid (aβ) at 1 h after administration, and it has the potential for the treatment of AD, and it is currently in the phase II clinical study stage (Alzheimers Dement. 2021, 17 (8), 1365-1382). However, CT1812 suffers from poor sigma-1 and sigma-2 receptor selectivity and poor oral bioavailability.

Therefore, there is an urgent need to investigate a compound capable of effectively inhibiting the sigma-2 receptor activity and its preparation.

SUMMARY

The object of the present invention is to provide an isoindol-sulfilimine compound and its preparation and use as a sigma-2 receptor inhibitor in order to overcome the above mentioned defects of the prior art, which is able to effectively inhibit the sigma-2 receptor activity by binding to the sigma-2 receptor and metamorphically modulating the sigma-2 receptor complex, and can be further used for the preparation of new therapeutic drugs for tumor and neurodegenerative diseases.

The object of the present invention can be achieved by the following technical solutions:

The first aspect of the present invention provides an isoindol-sulfilimine compound or a stereoisomer, solvate, or a pharmaceutically acceptable salt thereof, characterized in that said isoindol-sulfilimine compound has the chemical structural formula shown in formula (I):

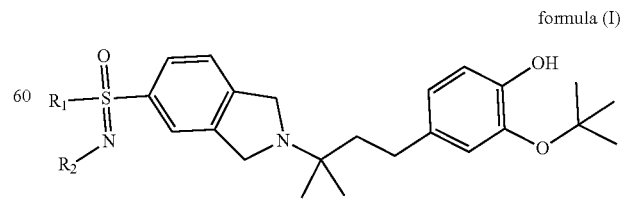

formula (I)

wherein $R_1$ is an alkyl group of 1-4 carbon atoms or an alkyl halide group of 1-4 carbon atoms; and $R_2$ is one of hydrogen, an alkyl group of 1-4 carbon atoms, an alkyl halide group of 1-4 carbon atoms and an acyl group of 1-4 carbon atoms.
In some embodiments, wherein, isoindol-sulfilimine compound is one of the following compounds 1-22:
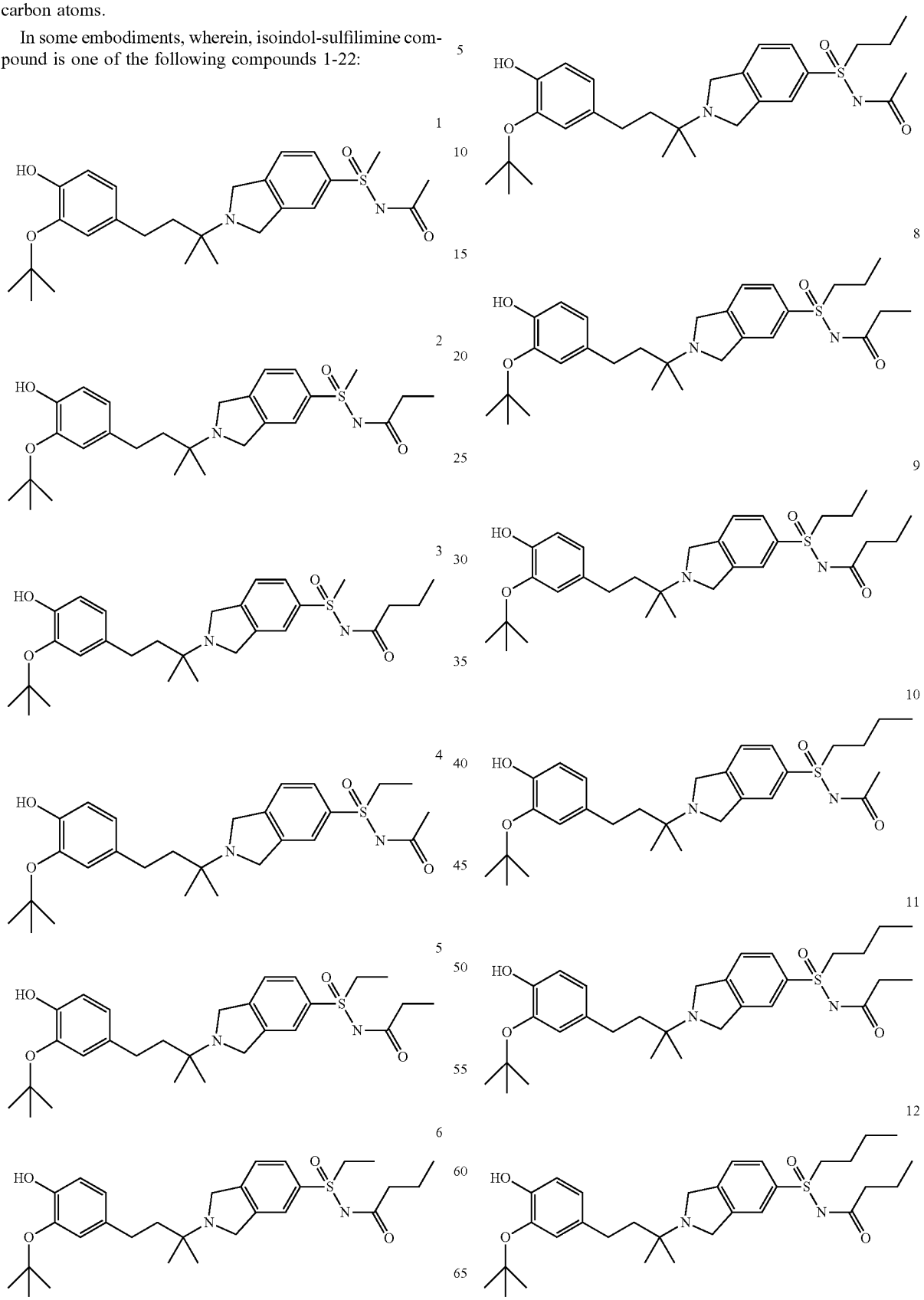

13
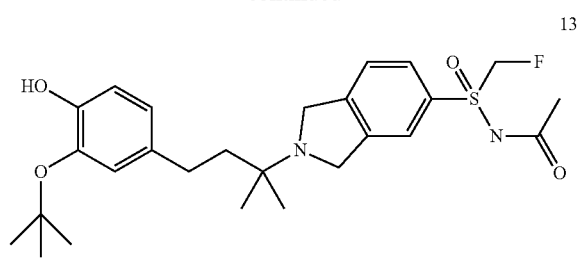

14
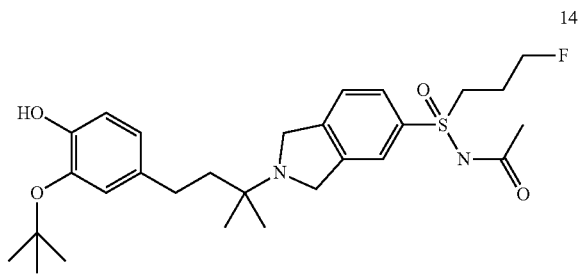

15
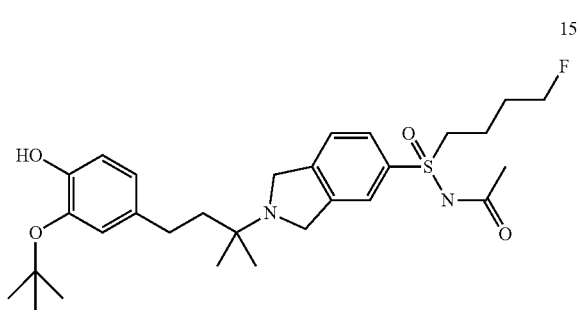

16
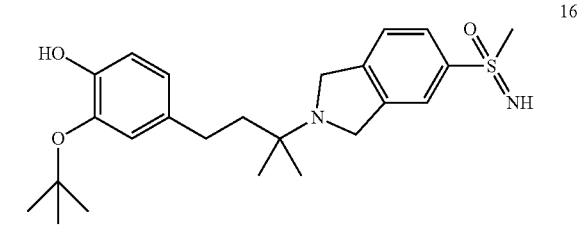

17
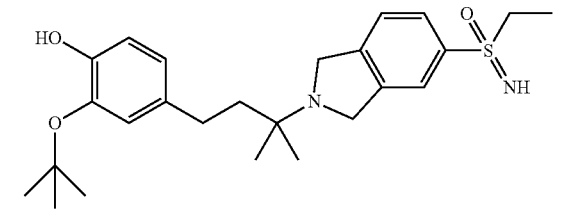

18
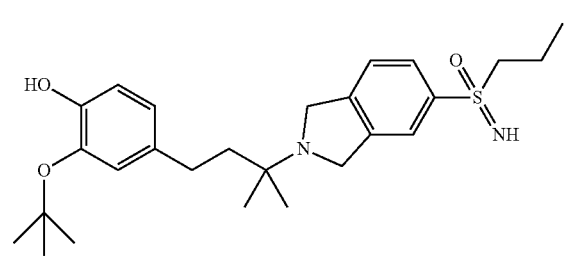

19
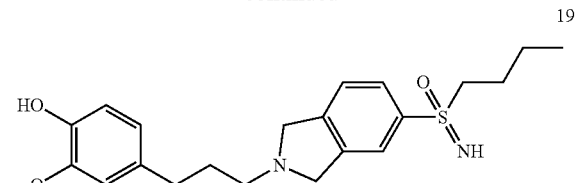

20
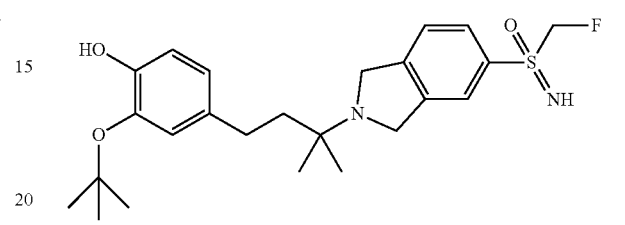

21
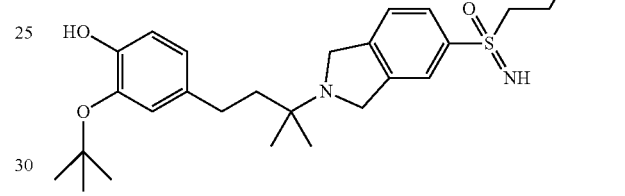

22
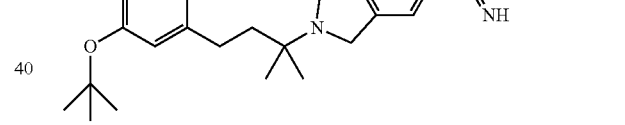

Compared with the prior art, the present invention has the following advantages and beneficial effects:

When the isoindol-sulfilimine compounds prepared by the present invention can effectively inhibit the sigma-2 receptor activity by binding to the sigma-2 receptor and deformationally regulating the sigma-2 receptor complex, which will lead to the instability of the binding of adjacent Aβ oligomers to the receptor on the synapse, thus leading to the removal of AB oligomers from the synapse. It can be further used for the preparation of new therapeutic drugs for tumor and neurodegenerative diseases.

As used herein, "pharmaceutically acceptable salt" refers to derivatives of the disclosed compounds wherein the parent compound is altered by converting an existing acid or base moiety into its salt form (e.g., by reacting the free base with a suitable organic acid). Examples of pharmaceutically acceptable salts include, but are not limited to, inorganic or organic acid salts of basic residues such as amines; base or organic salts of acidic residues such as carboxylic acids, and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, hydrobromide, hydrochloride, hydroiodide, 2-hydroxy-ethanesulfonate, lactate, laurate, lauryl sulfate, malate, maleate, malonate, methanesulfonate, 2-naphthalenesulfonate, nicotinate, nitrate, oleate, oxalate, palmitate, hexadecanoate, pectate, 3-phenylpropionate, phosphate, picrate, pivalate, propionate, stearate, succinate, sulfate, tartrate, thiocyanate, tosylate, undecanoate, trifluoroacetate, valerate salts and the like.

DESCRIPTION OF EMBODIMENTS

Embodiments

Specific embodiments of the present invention are described in detail below by means of embodiments, which are carried out on the premise of the program described herein, and detailed embodiments and specific operating procedures are given, but the scope of protection of the present invention is not limited to the following embodiments.

The present invention is further elaborated in the following with specific embodiments. Features such as component models, material names, connection structures, preparation means, materials, structures or composition ratios, etc., if not explicitly stated in the present technical solution, are regarded as common technical features disclosed in the prior art.

The present invention provides an isoindol-sulfilimine compound, said isoindol-sulfilimine compound having a chemical structural formula as shown in formula (I):

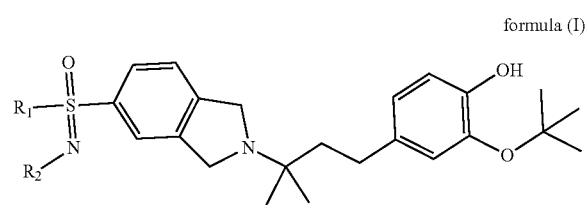

formula (I)

wherein $R_1$ is an alkyl group of 1-4 carbon atoms or an alkyl halide group of 1-4 carbon atoms; and $R_2$ is one of hydrogen, an alkyl group of 1-4 carbon atoms, an alkyl halide group of 1-4 carbon atoms, or an acyl group of 1-4 carbon atoms.

The present invention also provides a method of preparing an isoindol-sulfilimine compound, comprising the following steps:

Step A: dissolve catechol in dichloromethane, add catalytic amount of concentrated sulfuric acid at −30° C., then slowly add isobutene dropwise, slowly return to room temperature and then stirring overnight, add triethylamine to quench the reaction solution at −30° C., the reaction solution was evaporated to dryness and separated by column chromatography to obtain brownish yellow oil A; dissolve the oil A in methanol, add potassium iodide, sodium hydroxide, and then slowly add sodium hypochlorite dropwise at 0° C. Added saturated ammonium chloride to the reaction solution after the reaction at 0° C. for 3 h, extract with ethyl acetate, evaporate to brown oil B; dissolve oil B in triethylamine, then add 2-methylbut-3-yn-2-amine, bis(triphenylphosphine) palladium chloride, cuprous iodide, and then react under the protection of nitrogen for 3 h, then the reaction solution can be directly filtered and evaporated, and then isolated by column chromatography to get the yellow solid C. Dissolve yellow solid C in ethanol, then add hydrazine hydrate, copper sulfate pentahydrate and neocuproine, reflux overnight and then extract with ethyl acetate, evaporate to dryness by column chromatography separation of yellow solid D. The reaction formula is shown in formula (II):

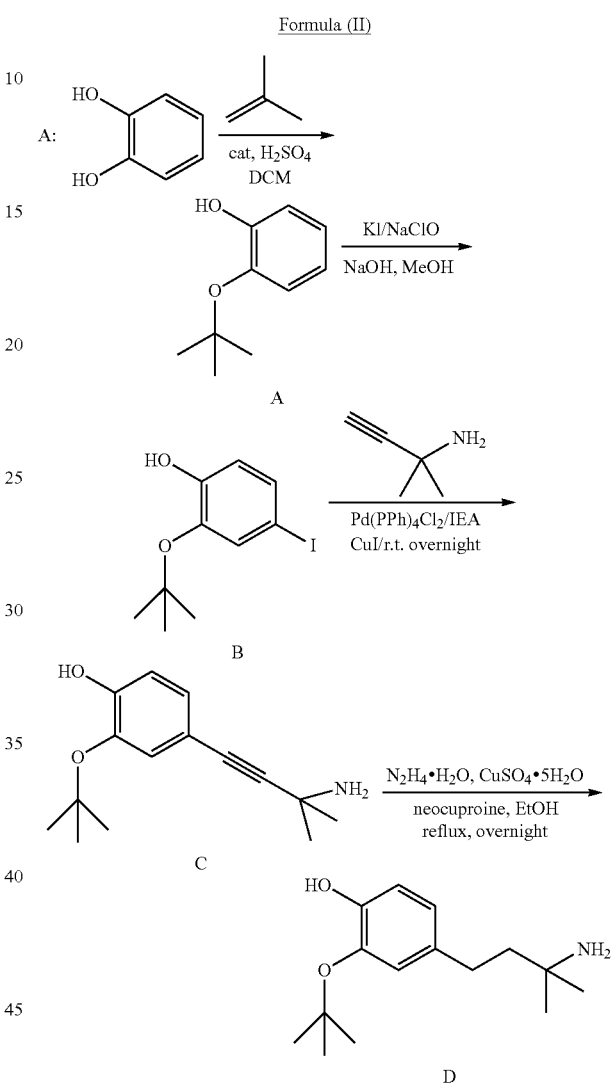

Step B: dissolve o-xylene in chloroform, slowly add chlorosulfonic acid dropwise at 0° C., after addition, stirring at room temperature for two days, the reaction solution was added to ice water, dichloromethane extraction, evaporated to obtain light yellow oil E; dissolve the oil E in xylene, add triphenylphosphine in batches, the reaction was carried out overnight at room temperature, evaporated to dryness, then add petroleum ether to remove excess triphenylphosphine at −10° C. with stirring, and evaporation of filtrate to separate yellow-green oil F; dissolve the yellow-green oil F in anhydrous ethanol, add sodium borohydride in batches, then add different alkyl-substituted or different fluoroalkyl-substituted halogenated hydrocarbons and react overnight, and the reaction solution was extracted by dichloromethane and directly put into the next step; add m-chloroperoxybenzoic acid to the above dichloromethane solution at −30° C., and then react for 3 h at this temperature, and then the reaction solution was recovered to room temperature, and add saturated sodium carbonate solution to adjust pH to neutral, dichloromethane extraction, solvent evaporation by column chromatography separation of light yellow oil G; light yellow oil G dissolved in methanol, then add ammonium carbamate, diacetyl iodobenzene stirred at room temperature for 30 min, the reaction solution was extracted with dichloromethane, evaporation by column chromatography separation of brown oil H; brown oil H dissolved in methylene chloride, then add triethylamine, and then slowly add different alkyl-substituted and different fluoroalkyl-substituted acyl chlorides dropwise at 0° C., and then directly evaporate after moving to room temperature for 1 h, and then purified by column chromatography to obtain OIL I. Dissolve OIL I in 1,2-dichloroethane, and then add N-bromosubstituted succinimide and azobisisobutyronitrile, and then reflux the reaction under nitrogen overnight, and then extracted by methylene chloride, and then purified by column chromatography to obtain the brown oil J. The last obtained brown oil J was separated by column chromatography, and the reaction solution was extracted by dichloromethane. The final brown oil J and the yellow solid D obtained in step A were dissolved in tetrahydrofuran, then triethylamine was added, and the reaction was carried out at 50° C. for 18 h under the protection of nitrogen, then suction filtered, and the filtrate was evaporated and separated by column chromatography to obtain the light brown oil, then potassium carbonate was added, and refluxed at 70° C. for 1.5 h. The target compounds were extracted with ethyl acetate, and then purified by column chromatography and pre-HPLC. The reaction formula was shown in formula (III):

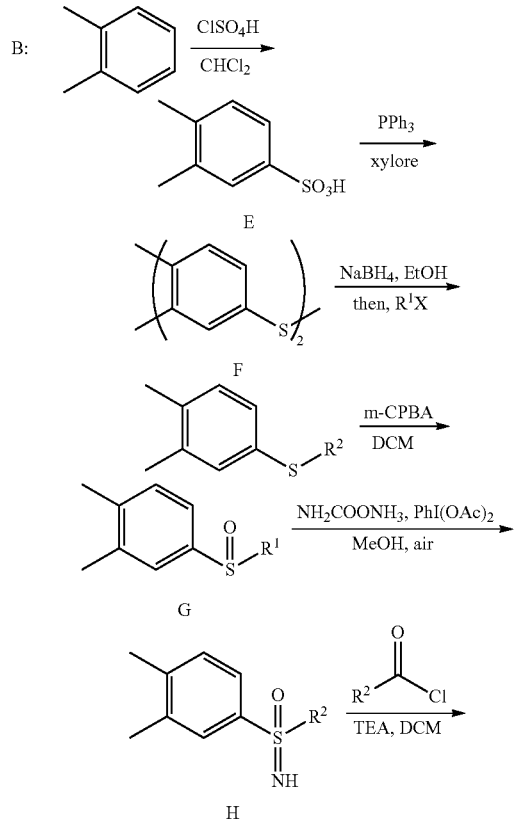

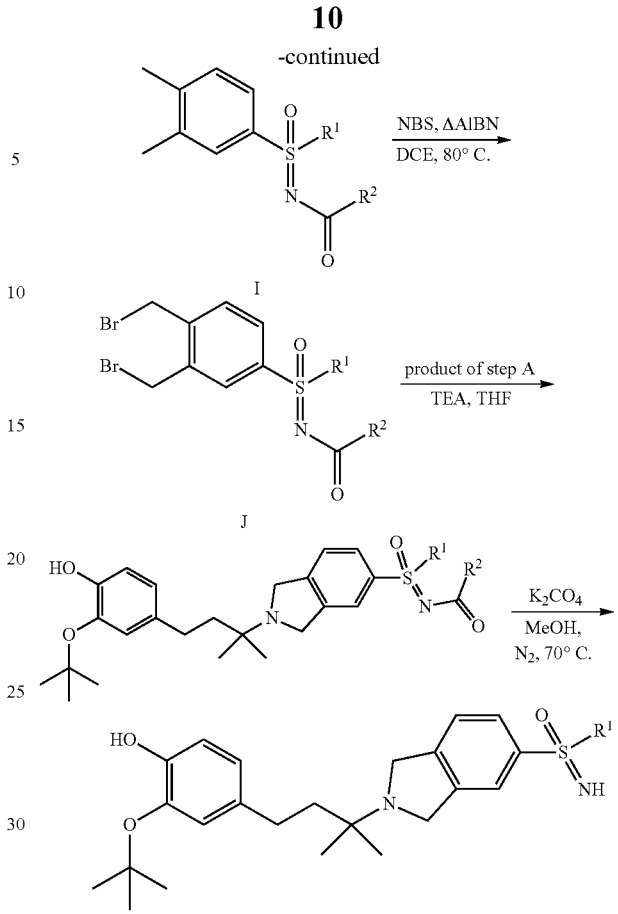

Example 1

The present embodiment provides a method for the preparation of Compound 1, N-((2-(4-(3-(tert-butoxy)-4-hydroxyphenyl)-2-methylbutan-2-yl)isoindol-5-yl)(methyl)(oxo)-λ6-thioimido)acetamide.

Step A:

Step 1: Catechol (30.00 g, 272.45 mmol) and dichloromethane (150 ml) were added to a 500 ml three-necked flask, followed by the addition of a catalytic amount of concentrated sulfuric acid (1.4 ml) at −35° C., followed by the slow dropwise addition of freshly prepared isobutene (152.62 g, 2720 mmol). After the dropwise addition, the reaction solution was gradually brought to room temperature overnight. The reaction solution was quenched by adding 3 ml of triethylamine to the reaction solution, which was evaporated to dryness and separated by column chromatography (EA/PE=1:10) to give 30 g of brownish-yellow oleyl A. Yield: 65.60%. LC-MS (ESI): m/z [M+H]+calcd for $C_{10}H_{14}NaO_2$ 189.1; found 189.1.

Step 2: Add brown oil A (14.00 g, 84.23 mmol), potassium iodide (13.98 g), sodium hydroxide (3.37 g, 84.23 mmol) and methanol (80 ml) into a 500 ml three-necked bottle, sodium hypochlorite (83.86 ml, 84.23 mmol) was slowly dropped at 0° C. for 1 hour, and then reacted at 0° C. for 3 hours. Add 250 ml of saturated ammonium chloride solution to the reaction solution, extract with ethyl acetate (250 ml×2), wash once with saturated brine (400 ml), dry with anhydrous sodium sulfate, evaporate to obtain 23.8 g of brown oil B, yield 96.71%. LC-MS (ESI): m/z [M−H]-calcd for $C_{10}H_{12}IO_2$ 291.0; found 291.0.

Step 3: Add brown oil B (3.30 g, 11.30 mmol), 2-methylbut-3-yn-2-amine (1.32 g, 15.82 mmol), bis(triphenylphosphine) palladium chloride (0.16 g, 0.226 mmol), cuprous iodide (0.11 g, 0.57 mmol), and triethylamine (40 ml) to a 100 ml vial. The reaction was carried out under nitrogen protection for 3 h. The reaction solution was directly evaporated and filtered, and separated by column chromatography (EA/PE=1:4) to give 2.38 g of yellow solid C, yield: 85.00%. LC-MS (ESI): m/z [M+H]+calcd for $C_{15}H_{26}NO_2$ 248.1; found 248.1.

Step 4: Yellow solid C (0.3 g, 1.2 mmol), hydrazine hydrate (0.3 g, 4.9 mmol), copper sulfate pentahydrate (30 mg, 0.12 mmol), neocuproine (25 mg, 0.12 mmol), and anhydrous ethanol (10 ml) were added to a 50 ml vial and the reaction was carried out at reflux for 18 h in vacuo. The reaction solution was cooled to room temperature and added with 20 ml of water, extracted with ethyl acetate (15 ml×3), washed once with saturated brine (50 ml) and dried with anhydrous sodium sulfate. Separated by column chromatography (EA/PE=1:1), 0.20 g of yellow solid D was obtained, yield: 66.67%. LC-MS (ESI): m/z [M+H]+calcd for $C_{15}H_{26}NO_2$ 252.1; found 252.1.

Step B:

Step 1:0-xylene (7, 30 g, 282.59 mmol) and chloroform (90 ml) were added to a 500 ml vial, then chlorosulfonic acid (72.55 g, 721.70 mmol) was added slowly dropwise at 0° C. After the dropwise addition, the reaction solution was gradually brought back to room temperature and stirred for two days. The reaction solution was slowly added to ice water, extracted with dichloromethane (200 ml×3), washed once with saturated brine (500 ml) and dried over anhydrous sodium sulfate. The solvent was evaporated to give 54.30 g of light yellow oil E, yield: 94.00%. LC-MS (ESI): m/z [M+H]+calcd for $C_8H_{11}O_3S$ 187.0; found 187.1.

Step 2: Add light yellow oil E (10.00 g, 48.90 mmol) and xylene (80 ml) to a 250 ml single-necked vial, then add triphenylphosphine (38.00 g, 146.60 mmol) in batches at 0° C., and then return the reaction solution to room temperature overnight. After the reaction solution was evaporated to dryness, 80 ml of petroleum ether was added, and the excess triphenylene was removed by filtration after stirring for 30 min at −10° C. The filtrate was evaporated to dryness and then separated by column chromatography (100% PE) to give 5.80 g of yellowish green oil F, yield: 86.60%. LC-MS (ESI): m/z [M+H]+calcd for $C_{16}H_{18}S_2$ 275.1; found 275.1

Step 3: F (0.5 g, 1.82 mmol) and anhydrous ethanol (20 ml) were added into a 100 ml double-necked flask, then sodium borohydride (0.21 g, 5.47 mmol) was added to the reaction solution in batches at 0° C., after stirring for 30 min, iodomethane (0.57 g, 4.00 mmol) was added, and the reaction solution was brought to room temperature for 3 h. The reaction solution was poured into 20 ml of saturated ammonium chloride, extracted with dichloromethane (20 ml×3), washed once with saturated salt water (50 ml), dried with anhydrous sodium sulfate, and the filtrate was pumped into a double-mouth flask and directly injected into the next reaction.

Step 4: The above filtrate was cooled to −30° C., then m-chloroperoxybenzoic acid (0.63 g, 3.61 mmol) was added in batches, and then reacted at this temperature for 3 h. The reaction solution was gradually brought back to room temperature, and the pH was adjusted to neutral by adding saturated sodium carbonate solution, and then the reaction solution was transferred to a partition funnel, extracted with dichloromethane (50 ml×3), washed once with saturated saline (150 ml) and dried over anhydrous sodium sulfate. The solvent was evaporated to dryness and separated by column chromatography (EA/PE=2:3) to give 0.45 g of light yellow oil G. Yield: 73.77%. LC-MS (ESI): m/z [M+H]+ calcd for $C_9H_{13}OS$ 169.1; found 169.1.

Step 5: To a 100 ml single-necked flask was added light yellow oil G (2.30 g, 13.67 mmol), ammonium carbamate (4.27 g, 54.68 mmol), diacetyl iodobenzene (13.20 g, 41.01 mmol), and methanol (45 ml), and then stirred at room temperature for 30 min. The reaction solution was poured into a saturated sodium bicarbonate solution. It was extracted with dichloromethane (50 ml×3), washed once with saturated brine (100 ml) and dried with anhydrous sodium sulfate. Separated by column chromatography (EA/PE=1:1) yielded 2.00 g of brown oil H, yield: 79.83%. LC-MS (ESI): m/z [M+H]+calcd for $C_9H_{14}NOS$ 184.1; found 184.1.

Step 6: Add brown oil H (0.50 g, 2.73 mmol), triethylamine (0.36 g, 3.55 mmol) and anhydrous dichloromethane (15 ml) in a 100 ml vial with nitrogen displacement, and slowly add acetyl chloride (0.26 g, 3.28 mmol) dropwise when the temperature of the reaction solution was reduced to 0° C., and transfer the reaction solution to room temperature after dropwise reaction for 1 h. Evaporate the reaction solution directly to dryness and purify by column chromatography (EA/PE=1:4) to obtain 0.59 g of white oil I. Yield: 95.92%. LC-MS (ESI): m/z [M+H]+calcd for $C_{11}H_{16}NO_2S$ 226.1; found 226.1

Step 7: I (0.30 g, 1.33 mmol), N-bromosuccinimide (0.57 g, 3.19 mmol), azobisisobutyronitrile (21.84 mg, 0.13 mmol) and 1,2-dichloroethane (20 ml) were added to a 50 ml single-necked vial, and the reaction was refluxed overnight with nitrogen displacement. After the reaction solution was cooled to room temperature, it was poured into water, extracted with dichloromethane (20 ml×3), washed once with saturated saline (50 ml) and dried over anhydrous sodium sulfate. Separated by column chromatography (EA/PE=1:4) yielded 0.26 g of brown oil J, yield: 51.82%.

Step 8: In a 50 ml vial, brown oil J (0.13 g, 0.52 mmol), yellow solid D (0.23 g, 0.59 mmol) obtained in step A, triethylamine (0.16 g, 1.57 mmol) and tetrahydrofuran (15 ml) were added and reacted under nitrogen protection at 50° C. for 18 h. After the reaction solution was cooled down to room temperature, the filtrate was extracted and evaporated directly to dryness. The filtrate was directly evaporated and separated by column chromatography (EA/DCM=1:4) to give 0.15 g of light brown oil, yield: 60.00%. Further purified by pre-HPLC (C18 column, ACN: 0.1% TFA 10%~60% gradient elution), 120 mg of trifluoroacetate of target compound 1 was obtained, yield: 39.12%.

The structural formula of compound 1 is shown below:

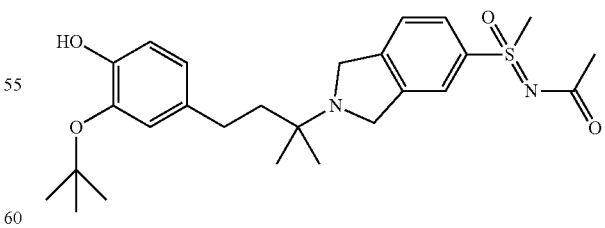

NMR and MS data for compound 1 are shown below:

$^1$H NMR (400 MHz, Chloroform-d) δ 7.91 (s, 1H), 7.82 (s, 1H), 7.48 (d, J=8.1 Hz, 1H), 6.87 (d, J=8.1 Hz, 1H), 6.85 (d, J=2.2 Hz, 1H), 6.78 (dd, J=8.2, 2.1 Hz, 1H), 4.99 (s, 2H), 4.53 (s, 2H), 3.27 (s, 3H), 2.71-2.58 (m, 2H), 2.13 (s, 3H), 2.08-1.96 (m, 2H), 1.51 (s, 6H), 1.40 (s, 9H).

¹³C NMR (101 MHZ, Chloroform-d) δ 180.82, 148.56, 142.24, 139.77, 139.52, 135.39, 131.11, 124.26, 123.68, 122.31, 115.06, 80.85, 64.86, 52.47, 52.38, 44.14, 39.68, 29.79, 28.85, 26.57, 22.05

LC-MS (ESI): m/z [M+H]+calcd for $C_{26}H_{37}N_2O_4S$ 473.2; found 473.2

Example 2

This embodiment provides a method for the preparation of compound 2, N-((2-(4-(3-(tert-butoxy)-4-hydroxyphenyl)-2-methylbutan-2-yl)isoindol-5-yl)(methyl)(oxo)-26-thioimido) propionamide. Referring to the method for the preparation of the compound of Example 1, unlike Example 1, the sixth step in Step B uses propionyl chloride as the raw material, and the rest of the steps are the same as those of Example 1, the trifluoroacetic acid salt 112 mg of Compound 2 was prepared and obtained as a white solid.

The structural formula of compound 2 is shown below:

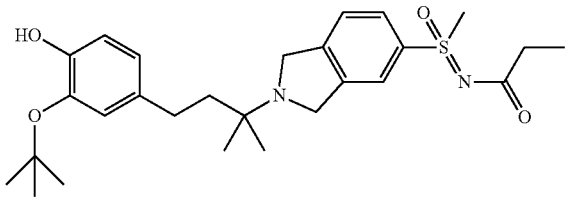 [SMILES: CCC(=O)N=S(C)(=O)c1ccc2c(c1)CN(C(C)(C)CCc1ccc(O)c(OC(C)(C)C)c1)C2]

NMR and MS data for compound 2 are shown below:

¹H NMR (400 MHZ, Chloroform-d) δ 7.91 (s, 1H), 7.82 (s, 1H), 7.48 (d, J=8.1 Hz, 1H), 6.87 (d, J=8.1 Hz, 1H), 6.85 (d, J=2.2 Hz, 1H), 6.78 (dd, J=8.1, 2.1 Hz, 1H), 4.99 (s, 2H), 4.54 (s, 2H), 3.26 (s, 3H), 2.71-2.58 (m, 2H), 2.41 (q, J=7.5 Hz, 2H), 2.08-1.93 (m, 2H), 1.51 (s, 6H), 1.40 (s, 9H), 1.09 (t, J=7.5 Hz, 3H).

¹³C NMR (101 MHz, Chloroform-d) δ 183.93, 148.64, 142.31, 140.13, 139.61, 135.52, 131.27, 124.34, 123.78, 122.43, 115.14, 80.92, 64.78, 52.49, 52.40, 44.30, 39.70, 32.71, 29.90, 28.95, 22.12, 9.64.

LC-MS (ESI): m/z [M+H]+calcd for $C_{27}H_{38}N_2O_4S$ 487.2; found 487.2

Example 3

This embodiment provides a method for the preparation of compound 3, N-((2-(4-(3-(tert-butoxy)-4-hydroxyphenyl)-2-methylbutan-2-yl)isoindol-5-yl)(methyl)(oxo)-26-thioimido) butanamide. Referring to the method for the preparation of the compound of Example 1, unlike Example 1, the sixth step of Step B uses butyryl chloride as the raw material, and the rest of the steps are the same as those of Example 1, the trifluoroacetate salt of Compound 3, 84 mg, a white solid, was prepared and obtained.

The structural formula of compound 3 is shown below:

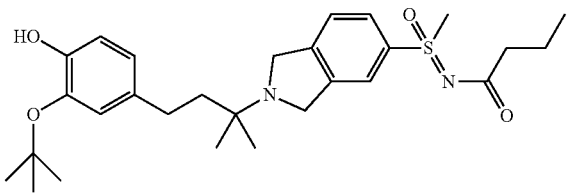 [SMILES: CCCC(=O)N=S(C)(=O)c1ccc2c(c1)CN(C(C)(C)CCc1ccc(O)c(OC(C)(C)C)c1)C2]

NMR and MS data for compound 3 are shown below:

¹H NMR (400 MHZ, Chloroform-d) δ 7.87 (s, 1H), 7.80 (s, 1H), 7.45 (d, J=8.1 Hz, 1H), 6.84 (d, J=8.1 Hz, 1H), 6.82 (d, J=2.2 Hz, 1H), 6.75 (dd, J=8.2, 2.1 Hz, 1H), 4.97 (s, 2H), 4.54 (s, 2H), 3.24 (s, 3H), 2.69-2.54 (m, 2H), 2.32 (t, J=7.4 Hz, 2H), 2.06-1.93 (m, 2H), 1.59 (p, J=7.4 Hz, 2H), 1.49 (s, 6H), 1.38 (s, 9H), 0.90 (t, J=7.4 Hz, 3H).

¹³C NMR (101 MHZ, Chloroform-d) δ 183.28, 148.63, 142.31, 140.17, 139.61, 135.52, 131.27, 124.33, 123.78, 122.41, 115.13, 80.92, 64.75, 52.48, 52.38, 44.30, 41.50, 39.70, 29.91, 28.95, 22.13, 19.03, 13.89.

LC-MS (ESI): m/z [M+H]+calcd for $C_{28}H_{40}N_2O_4S$ 501.2; found 501.2.

Example 4

This embodiment provides a method for the preparation of a compound 4, N-((2-(4-(3-(tert-butoxy)-4-hydroxyphenyl)-2-methylbutan-2-yl)isoindol-5-yl)(ethyl)(oxo)-26-thioimido)acetamide. Referring to the method for the preparation of the compound of Example 1, differing from Example 1 in that ethyl iodide was used as a raw material in the third step of Step B, acetyl chloride was used as a raw material in the sixth step of Step B, and the rest of the steps were the same as those of Example 1, the trifluoroacetate salt of Compound 4, 243 mg, a white solid, was obtained by the preparation.

The structural formula of compound 4 is shown below:

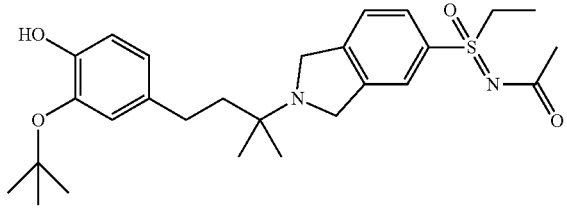 [SMILES: CCS(=O)(=NC(C)=O)c1ccc2c(c1)CN(C(C)(C)CCc1ccc(O)c(OC(C)(C)C)c1)C2]

NMR and MS data for compound 4 are shown below:

¹H NMR (400 MHZ, Chloroform-d) δ 8.02-7.60 (m, 2H), 7.48 (d, J=8.1 Hz, 1H), 6.87 (d, J=8.1 Hz, 1H), 6.85 (d, J=2.1 Hz, 1H), 6.78 (dd, J=8.3, 2.0 Hz, 1H), 4.99 (s, 2H), 4.54 (s, 2H), 3.51-3.18 (m, 2H), 2.72-2.52 (m, 2H), 2.13 (s, 3H), 2.09-1.97 (m, 2H), 1.52 (s, 7H), 1.41 (d, J=1.0 Hz, 10H), 1.24 (t, J=7.3 Hz, 4H).

¹³C NMR (101 MHZ, Chloroform-d) δ 180.88, 148.63, 142.31, 139.60, 137.70, 135.48, 131.24, 124.27, 123.77, 122.39, 115.13, 80.93, 64.78, 52.49, 52.39, 50.60, 39.81, 29.87, 28.95, 26.68, 22.18, 6.71

LC-MS (ESI): m/z [M+H]+calcd for $C_{27}H_{39}N_2O_4S$ 487.2; found 487.2.

Example 5

This embodiment provides a method for the preparation of a compound 5, N-((2-(4-(3-(tert-butoxy)-4-hydroxyphenyl)-2-methylbutan-2-yl)isoindol-5-yl)(ethyl)(oxo)-16-thioimido) propionamide. Referring to the method for the preparation of the compound of Example 1, differing from Example 1 in that ethyl iodide was used as a raw material in the third step of Step B, propionyl chloride was used as a raw material in the sixth step of Step B, and the rest of the steps were the same as those of Example 1, a trifluoroacetic acid salt of Compound 5, 100 mg, a white solid, was obtained by the preparation.

The structural formula of compound 5 is shown below:

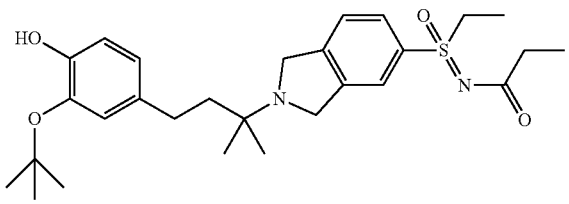 [SMILES: CCC(=O)N=S(=O)(CC)c1ccc2c(c1)CN(C(C)(C)CCc1ccc(O)c(OC(C)(C)C)c1)C2]

NMR and MS data for compound 5 are shown below:
$^1$H NMR (400 MHz, Chloroform-d) δ 7.86 (s, 1H), 7.76 (s, 1H), 7.47 (d, J=8.0 Hz, 1H), 6.87 (d, J=8.1 Hz, 1H), 6.85 (d, J=2.2 Hz, 1H), 6.78 (dd, J=8.2, 2.0 Hz, 1H), 4.98 (s, 2H), 4.53 (s, 2H), 3.53-3.19 (m, 2H), 2.71-2.57 (m, 2H), 2.41 (q, J=7.5 Hz, 2H), 2.11-1.95 (m, 2H), 1.51 (s, 6H), 1.41 (s, 9H), 1.23 (t, J=7.3 Hz, 3H), 1.10 (t, J=7.5 Hz, 3H).
$^{13}$C NMR (101 MHZ, Chloroform-d) δ 183.97, 148.62, 142.31, 139.59, 137.95, 135.50, 131.30, 124.26, 123.78, 122.41, 115.12, 80.91, 64.64, 52.43, 52.34, 50.60, 39.75, 32.75, 29.89, 28.95, 22.17, 9.75, 6.80.
LC-MS (ESI): m/z [M+H]+calcd for $C_{28}H_{41}N_2O_4S$ 501.2; found 501.2.

Example 6

This embodiment provides a method for the preparation of Compound 6, N-((2-(4-(3-(tert-butoxy)-4-hydroxyphenyl)-2-methylbutan-2-yl)isoindol-5-yl)(ethyl)(oxo)-26-thioimido) butyramide, with reference to the method of preparing the compound of Example 1, and differing from Example 1 in that the third step of Step B uses ethyl iodide as the raw material, and the step 6 used butyryl chloride as the raw material, and the remaining steps were the same as that of Example I. The trifluoroacetate salt 112 mg of compound 6 was prepared, a white solid.

The structural formula of compound 6 is shown below:

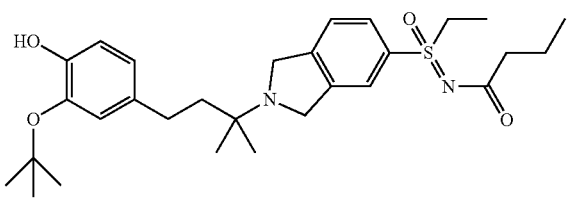 [SMILES: CCCC(=O)N=S(=O)(CC)c1ccc2c(c1)CN(C(C)(C)CCc1ccc(O)c(OC(C)(C)C)c1)C2]

NMR and MS data for compound 6 are shown below:
$^1$H NMR (400 MHZ, Chloroform-d) δ 7.87 (s, 1H), 7.76 (s, 1H), 7.47 (d, J=8.1 Hz, 1H), 6.87 (d, J=8.1 Hz, 1H), 6.85 (d, J=2.6 Hz, 1H), 6.78 (dd, J=8.2, 2.0 Hz, 1H), 4.99 (s, 2H), 4.53 (s, 2H), 3.37 (p, J=7.3 Hz, 2H), 2.73-2.57 (m, 2H), 2.35 (t, J=7.4 Hz, 2H), 2.08-1.97 (m, 2H), 1.64 (q, J=7.4 Hz, 2H), 1.51 (s, 6H), 1.41 (d, J=0.9 Hz, 9H), 1.23 (t, J=7.3 Hz, 3H), 0.93 (t, J=7.4 Hz, 3H).
$^{13}$C NMR (101 MHz, Chloroform-d) δ 183.20, 148.62, 142.32, 139.61, 138.02, 135.52, 131.31, 124.22, 123.76, 122.38, 115.11, 80.89, 64.58, 52.41, 52.31, 50.61, 41.56, 39.73, 29.90, 28.96, 22.17, 19.12, 13.92, 6.82.
LC-MS (ESI): m/z [M+H]+calcd for $C_{29}H_{43}N_2O_4S$ 515.2; found 515.2.

Example 7

The present embodiment provides a method for the preparation of Compound 7, N-((2-(4-(3-(tert-butoxy)-4-hydroxyphenyl)-2-methylbutan-2-yl)isoindol-5-yl)(propyl)(oxo)-26-thioimino)acetamide. Referring to the method for the preparation of the compound of Example 1, Unlike Example 1, the third step of Step B uses bromopropane as the raw material, and the sixth step of Step B uses acetyl chloride as the raw material, the rest of the steps are the same as that of Example 1, was prepared to obtain 233 mg of the trifluoroacetate salt of Compound 7, a white solid.

The structural formula of compound 7 is shown below:

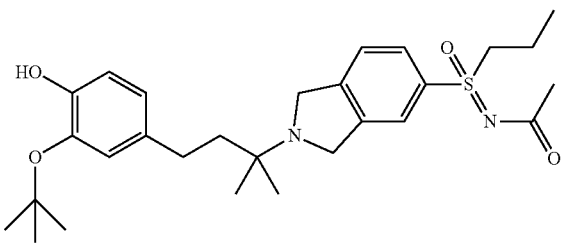 [SMILES: CCCS(=O)(=NC(C)=O)c1ccc2c(c1)CN(C(C)(C)CCc1ccc(O)c(OC(C)(C)C)c1)C2]

NMR and MS data for compound 7 are shown below:
$^1$H NMR (400 MHZ, Chloroform-d) δ 7.87 (s, 1H), 7.79 (s, 1H), 7.48 (d, J=8.1 Hz, 1H), 6.87 (d, J=8.2 Hz, 1H), 6.85 (d, J=2.0 Hz, 1H), 6.78 (dd, J=8.2, 2.1 Hz, 1H), 4.99 (s, 2H), 4.54 (s, 2H), 3.35 (ddd, J=14.0, 11.0, 5.2 Hz, 1H), 3.25 (ddd, J=14.1, 10.9, 5.2 Hz, 1H), 2.75-2.57 (m, 2H), 2.12 (s, 3H), 2.07-1.98 (m, 2H), 1.74 (dt, J=12.3, 6.3 Hz, 1H), 1.68-1.57 (m, 1H), 1.52 (s, 6H), 1.41 (s, 9H), 0.98 (t, J=7.4 Hz, 3H).
$^{13}$C NMR (101 MHZ, Chloroform-d) δ 180.91, 148.63, 142.31, 139.54, 138.30, 135.46, 131.24, 124.27, 123.78, 122.40, 115.14, 80.93, 64.78, 57.50, 52.49, 52.39, 39.81, 29.86, 28.95, 26.70, 22.18, 15.89, 12.59.
LC-MS (ESI): m/z [M+H]+calcd for $C_{28}H_{41}N_2O_4S$ 501.2; found 501.2.

Example 8

This embodiment provides a method for the preparation of compound 8, N-((2-(4-(3-(tert-butoxy)-4-hydroxyphenyl)-2-methylbutan-2-yl)isoindol-5-yl)(propyl)(oxo)-26-thioimido) propionamide. Referring to the method for the preparation of the compound of Example 1, differing from Example 1 in that the third step of Step B uses bromopropane as the raw material, the sixth step of Step B uses propionyl chloride as the raw material, and the rest of the steps are the same as those of Example 1, the trifluoroacetic acid salt of Compound 8, 112 mg, a white solid, was prepared.

The structural formula of compound 8 is shown below:

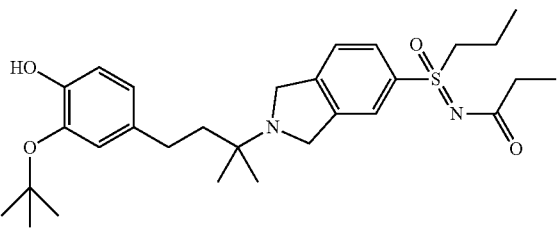 [SMILES: CCCS(=O)(=NC(=O)CC)c1ccc2c(c1)CN(C(C)(C)CCc1ccc(O)c(OC(C)(C)C)c1)C2]

NMR and MS data for compound 8 are shown below:
$^1$H NMR (400 MHZ, Chloroform-d) δ 7.88 (s, 1H), 7.70 (s, 1H), 7.44 (d, J=8.0 Hz, 1H), 6.85 (d, J=8.1 Hz, 1H), 6.82 (d, J=2.1 Hz, 1H), 6.75 (dd, J=8.2, 2.1 Hz, 1H), 4.96 (s, 2H), 4.45 (s, 2H), 3.32 (ddd, J=14.1, 10.9, 5.2 Hz, 1H), 3.23 (ddd, J=14.1, 10.9, 5.2 Hz, 1H), 2.69-2.54 (m, 2H), 2.38 (q, J=7.5 Hz, 2H), 2.05-1.94 (m, 2H), 1.81-1.64 (m, 1H), 1.64-1.52 (m, 1H), 1.49 (s, 6H), 1.38 (d, J=0.9 Hz, 9H), 1.07 (t, J=7.5 Hz, 3H), 0.95 (t, J=7.4 Hz, 3H).

$^{13}$C NMR (101 MHz, Chloroform-d) δ 183.97, 148.62, 142.31, 139.50, 138.61, 135.46, 131.28, 124.25, 123.77, 122.38, 115.12, 80.91, 64.64, 57.53, 52.43, 52.34, 39.77, 32.77, 29.89, 28.96, 22.18, 15.96, 12.63, 9.74.

LC-MS (ESI): m/z [M+H]+calcd for $C_{29}H_{43}N_2O_4S$ 515.2; found 515.2.

Example 9

The present embodiment provides a method for the preparation of compound 9, N-((2-(4-(3-(tert-butoxy)-4-hydroxyphenyl)-2-methylbutan-2-yl)isoindol-5-yl)(propyl)(oxo)-26-thioimido) butanamide. Referring to the method for the preparation of the compound of Example 1, Differing from Example 1, Step 3 of Step B uses bromopropane as the raw material, and Step 6 of Step B uses butyryl chloride as the raw material, The rest of the steps are the same as those of Example 1, The trifluoroacetic acid salt of Compound 9 was prepared and obtained as 55 mg of the compound, white solid.

The structural formula of compound 9 is shown below:

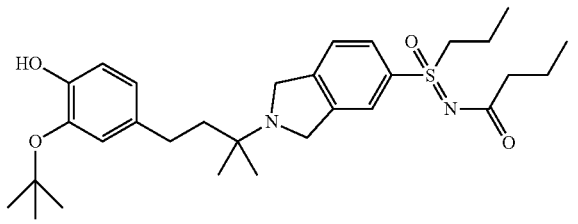 [SMILES: CCCC(=O)N=S(=O)(CCC)c1ccc2c(c1)CN(C(C)(C)CCc1ccc(O)c(OC(C)(C)C)c1)C2]

NMR and MS data for compound 9 are shown below:
$^1$H NMR (400 MHZ, Chloroform-d) δ 7.89 (s, 1H), 7.74 (s, 1H), 7.46 (d, J=8.1 Hz, 1H), 6.87 (dd, J=8.2, 0.9 Hz, 1H), 6.85 (d, J=2.0 Hz, 1H), 6.78 (dd, J=8.1, 2.0 Hz, 1H), 4.99 (s, 2H), 4.51 (s, 2H), 3.35 (ddd, J=15.9, 10.9, 5.2 Hz, 1H), 3.26 (td, J=14.4, 12.7, 5.3 Hz, 1H), 2.72-2.58 (m, 2H), 2.35 (t, J=7.4 Hz, 2H), 2.09-1.99 (m, 2H), 1.73 (q, J=6.7, 6.2 Hz, 1H), 1.62 (p, J=7.3 Hz, 3H), 1.51 (s, 6H), 1.41 (s, 9H), 0.98 (d, J=7.4 Hz, 3H), 0.92 (d, J=7.4 Hz, 3H).

$^{13}$C NMR (101 MHZ, Chloroform-d) δ 183.17, 148.61, 142.32, 139.54, 138.67, 135.50, 131.30, 124.21, 123.75, 122.35, 115.10, 80.89, 64.55, 57.55, 52.39, 52.30, 41.59, 39.74, 29.91, 28.97, 22.18, 19.11, 15.99, 13.92, 12.64.

LC-MS (ESI): m/z [M+H]+calcd for $C_{30}H_{45}N_2O_4S$ 529.2; found 529.2.

Example 10

The present embodiment provides a method for the preparation of Compound 10, N-((2-(4-(3-(tert-butoxy)-4-hydroxyphenyl)-2-methylbutan-2-yl)isoindol-5-yl)(butyl)(oxo)-26-thioimino)acetamide. Referring to the method for the preparation of the compound of Example 1, differing from Example 1 in that the third step of Step B uses bromobutane as the raw material, the sixth step of Step B uses acetyl chloride as the raw material, and the rest of the steps are the same as those of Example 1, the trifluoroacetic acid salt of Compound 10, 139 mg, a white solid, was obtained by the preparation.

The structural formula of compound 10 is shown below:

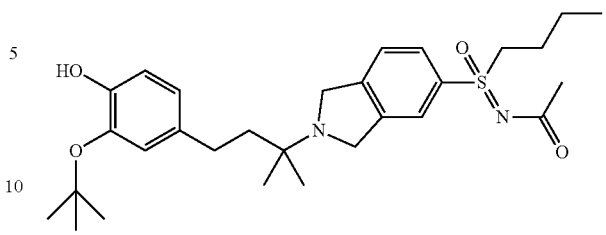

NMR and MS data for compound 10 are shown below:
$^1$H NMR (400 MHZ, Chloroform-d) δ 8.06-7.61 (m, 2H), 7.48 (d, J=8.0 Hz, 1H), 6.87 (d, J=8.2 Hz, 1H), 6.85 (d, J=2.1 Hz, 1H), 6.78 (dd, J=8.2, 2.1 Hz, 1H), 5.01 (s, 2H), 4.53 (s, 2H), 3.37 (ddd, J=13.9, 11.3, 4.9 Hz, 1H), 3.26 (ddd, J=14.0, 11.4, 5.0 Hz, 1H), 2.73-2.59 (m, 2H), 2.12 (s, 3H), 2.07-2.00 (m, 2H), 1.68 (tdd, J=12.5, 8.9, 5.0 Hz, 1H), 1.62-1.54 (m, 1H), 1.53 (s, 6H), 1.41 (s, 9H), 1.39-1.32 (m, 2H), 0.89 (t, J=7.3 Hz, 3H).

$^{13}$C NMR (101 MHZ, Chloroform-d) δ 180.80, 148.63, 142.31, 139.55, 138.37, 135.47, 131.26, 124.27, 123.77, 122.38, 115.13, 80.92, 64.73, 55.74, 52.46, 52.36, 39.80, 29.88, 28.95, 26.72, 23.82, 22.18, 21.37, 13.43.

LC-MS (ESI): m/z [M+H]+calcd for $C_{29}H_{43}N_2O_4S$ 515.2; found 515.2.

Example 11

This embodiment provides a method of preparing a compound 11, N-((2-(4-(3-(tert-butoxy)-4-hydroxyphenyl)-2-methylbutan-2-yl)isoindol-5-yl)(butyl)(oxo)-26-thioimido) propionamide. Referring to the method for the preparation of the compound of Example 1, differing from Example 1 in that the third step of Step B uses bromobutane as the raw material, the sixth step of Step B uses propionyl chloride as the raw material, and the remaining steps are the same as those of Example 1, a trifluoroacetic acid salt 90 mg of Compound 11, a white solid, was prepared.

The structural formula of compound 11 is shown below:

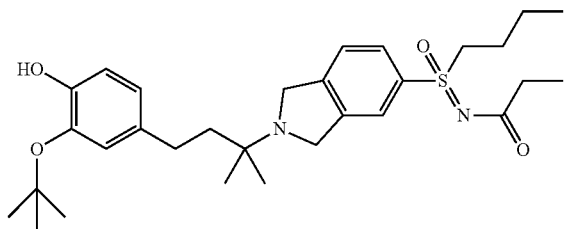 [SMILES: CCCCS(=O)(=NC(=O)CC)c1ccc2c(c1)CN(C(C)(C)CCc1ccc(O)c(OC(C)(C)C)c1)C2]

NMR and MS data for compound 11 are shown below:
$^1$H NMR (400 MHZ, Chloroform-d) δ 7.89 (s, 1H), 7.75 (s, 1H), 7.47 (d, J=8.1 Hz, 1H), 6.87 (d, J=8.1 Hz, 1H), 6.85 (d, J=2.1 Hz, 1H), 6.78 (dd, J=8.1, 2.1 Hz, 1H), 5.00 (s, 2H), 4.51 (s, 2H), 3.38 (ddd, J=15.9, 11.3, 4.9 Hz, 1H), 3.27 (ddd, J=14.1, 11.3, 4.9 Hz, 1H), 2.69-2.58 (m, 2H), 2.40 (q, J=7.5 Hz, 2H), 2.08-1.98 (m, 2H), 1.69 (dq, J=13.4, 6.8, 6.0 Hz, 1H), 1.55 (d, J=9.2 Hz, 1H), 1.51 (s, 7H), 1.41 (s, 10H), 1.39-1.30 (m, 2H).

$^{13}$C NMR (101 MHz, Chloroform-d) δ 183.85, 148.61, 142.31, 139.56, 138.65, 135.50, 131.32, 124.25, 123.77, 122.37, 115.11, 80.91, 64.52, 55.75, 52.38, 52.29, 39.74, 32.76, 29.91, 28.96, 23.91, 22.18, 21.39, 13.45, 9.74.

LC-MS (ESI): m/z [M+H]+calcd for C$_{30}$H$_{45}$N$_2$O$_4$S 529.2; found 529.2.

Example 12

The present embodiment provides a method for the preparation of Compound 12, N-((2-(4-(3-(tert-butoxy)-4-hydroxyphenyl)-2-methylbutan-2-yl)isoindol-5-yl)(butyl)(oxo)-26-thiimido) butyramide, with reference to the method for the preparation of the compound of Example I. Bromobutane was used as the raw material for the third step of Step B, and butyryl chloride was used as the raw material for the sixth step of Step B, The rest of the steps were the same as in Example 1, 82 mg of trifluoroacetate salt of compound 12 was prepared, white solid.

The structural formula of compound 12 is shown below:

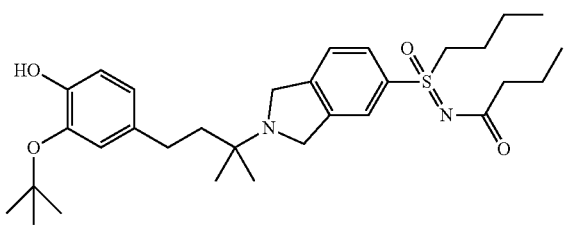 [SMILES: CCCCS(=O)(=NC(=O)CCC)c1ccc2c(c1)CN(C(C)(C)CCc1ccc(O)c(OC(C)(C)C)c1)C2]

NMR and MS data for compound 12 are shown below:

$^1$H NMR (400 MHZ, Chloroform-d) δ 7.88 (s, 1H), 7.69 (s, 1H), 7.45 (d, J=8.1 Hz, 1H), 6.85 (d, J=8.1 Hz, 1H), 6.83 (d, J=2.0 Hz, 1H), 6.76 (dd, J=8.1, 2.1 Hz, 1H), 4.97 (s, 2H), 4.49 (s, 2H), 3.35 (ddd, J=16.0, 11.2, 4.9 Hz, 1H), 3.25 (ddd, J=14.0, 11.3, 4.9 Hz, 1H), 2.68-2.55 (m, 2H), 2.32 (t, J=7.4 Hz, 2H), 2.06-1.95 (m, 2H), 1.75-1.52 (m, 4H), 1.49 (s, 7H), 1.38 (s, 10H), 1.37-1.28 (m, 2H), 0.90 (t, J=7.4 Hz, 3H), 0.86 (t, J=7.3 Hz, 3H).

$^{13}$C NMR (101 MHz, Chloroform-d) δ 183.30, 148.62, 142.31, 139.47, 138.67, 135.43, 131.27, 124.24, 123.76, 122.36, 115.11, 80.92, 64.64, 55.74, 52.43, 52.33, 41.56, 39.79, 29.90, 28.96, 23.89, 22.19, 21.38, 19.12, 13.92, 13.44.

LC-MS (ESI): m/z [M+H]+calcd for C$_{31}$H$_{47}$N$_2$O$_4$S 543.2; found 543.2.

Example 13

This embodiment provides a method for the preparation of compound 13, N-((2-(4-(3-(tert-butoxy)-4-hydroxyphenyl)-2-methylbutan-2-yl)isoindol-5-yl)(fluoromethyl)(oxo)-26-thioimido)acetamide. Referring to the method for the preparation of the compound of Example 1, differing from Example 1 in that the third step of Step B uses bromoiodomethane as the raw material, the sixth step of Step B uses acetyl chloride as the raw material, and the remaining steps are the same as those of Example 1, the trifluoroacetate salt of Compound 13, 145 mg, a white solid, was prepared.

The structural formula of the target compound 13 is shown below:

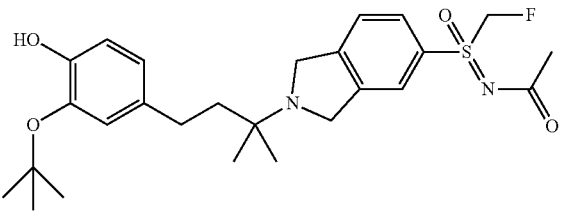 [SMILES: CC(=O)N=S(=O)(CF)c1ccc2c(c1)CN(C(C)(C)CCc1ccc(O)c(OC(C)(C)C)c1)C2]

NMR and MS data for the target compound 13 are shown below:

$^1$H NMR (400 MHZ, Chloroform-d) δ 8.05-7.79 (m, 2H), 7.52 (d, J=8.1 Hz, 1H), 6.86 (d, J=8.4 Hz, 1H), 6.85 (d, J=2.8 Hz, 1H), 6.77 (dd, J=8.1, 2.1 Hz, 1H), 5.71 (dd, J=46.3, 9.3 Hz, 1H), 5.37 (dd, J=46.8, 9.2 Hz, 1H), 5.04 (s, 2H), 4.57 (s, 2H), 2.70-2.57 (m, 2H), 2.20 (s, 3H), 2.08-1.96 (m, 2H), 1.51 (s, 6H), 1.40 (d, J=1.0 Hz, 9H).

$^{13}$C NMR (101 MHZ, Chloroform-d) δ 180.87, 148.65, 142.34, 140.91, 135.66, 134.97, 131.22, 129.83, 124.36, 123.74, 122.37, 115.14, 92.53, 90.28, 80.93, 64.93, 52.54, 52.35, 39.60, 29.89, 28.94, 26.81, 22.15. 19F NMR (376 MHz, Chloroform-d) 8-75.48 (s), −203.48 (t, J=47.4 Hz).

LC-MS (ESI): m/z [M+H]+calcd for C$_{26}$H$_{36}$FN$_2$O$_4$S 491.2; found 491.2.

Example 14

The present embodiment provides a method for the preparation of compound 14, N-((2-(4-(3-(tert-butoxy)-4-hydroxyphenyl)-2-methylbutan-2-yl)isoindol-5-yl)(fluoropropyl)(oxo)-16-thiimido)acetamide, with reference to the method of preparing the compound of Example 1, differing from Example 1 in that the third step of step B uses 1-fluoro-3-bromopropane as the raw material, the sixth step of Step B used acetyl chloride as raw material, and the remaining steps were the same as that of Example I. 197 mg of trifluoroacetate salt of Compound 14 was prepared, a white solid.

The structural formula of compound 14 is shown below:

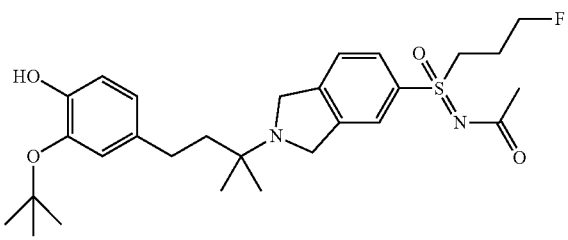 [SMILES: CC(=O)N=S(=O)(CCCF)c1ccc2c(c1)CN(C(C)(C)CCc1ccc(O)c(OC(C)(C)C)c1)C2]

NMR and MS data for compound 14 are shown below:

$^1$H NMR (400 MHZ, Chloroform-d) δ 7.90 (s, 1H), 7.77 (s, 1H), 7.49 (d, J=8.0 Hz, 1H), 6.87 (d, J=8.1 Hz, 1H), 6.85 (d, J=2.0 Hz, 1H), 6.78 (dd, J=8.1, 2.1 Hz, 1H), 5.84 (s, 2H), 4.98 (s, 2H), 4.53 (dd, J=6.6, 4.5 Hz, 1H), 4.41 (dd, J=6.6, 4.6 Hz, 1H), 3.53 (ddd, J=15.2, 10.4, 5.2 Hz, 1H), 3.39 (ddd, J=14.6, 10.3, 5.1 Hz, 1H), 2.69-2.60 (m, 2H), 2.13 (s, 4H), 2.07-1.91 (m, 3H), 1.52 (s, 6H), 1.41 (s, 9H).

$^{13}$C NMR (101 MHZ, Chloroform-d) δ 180.98, 148.65, 142.32, 139.71, 138.09, 135.59, 131.19, 124.44, 123.77, 122.39, 115.15, 82.02, 80.95, 80.34, 64.90, 52.53, 52.43, 39.88, 29.84, 28.94, 26.66, 23.63, 23.42, 22.19. 19F NMR (376 MHz, Chloroform-d) 8-75.61 (s), −220.65 (tt, J=46.9, 25.0 Hz).

LC-MS (ESI): m/z [M+H]+calcd for $C_{28}H_{40}FN_2O_4S$ 519.2; found 519.2.

Example 15

This embodiment provides a method for the preparation of compound 15, N-((2-(4-(3-(tert-butoxy)-4-hydroxyphenyl)-2-methylbutan-2-yl)isoindol-5-yl)(fluoro-butyl)(oxo)-26-thioimido)acetamide. Referring to the method for the preparation of the compound of Example 1, differs from Example 1 in that, the third step of Step B uses 1-fluoro-4-bromobutane as the raw material, the sixth step of Step B uses acetyl chloride as the raw material, and the rest of the steps are the same as those of Example 1, and the trifluoroacetate salt of Compound 15, 171 mg, a white solid, was prepared.

The structural formula of compound 15 is shown below:

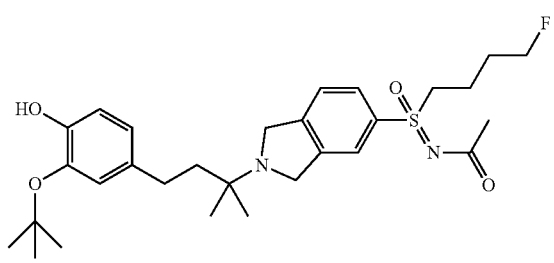 [SMILES: CC(=O)N=S(=O)(CCCCF)c1ccc2c(c1)CN(C(C)(C)CCc1ccc(O)c(OC(C)(C)C)c1)C2]

NMR and MS data for compound 15 are shown below:
$^1$H NMR (400 MHz, Chloroform-d) δ 7.85 (s, 2H), 7.48 (d, J=8.1 Hz, 1H), 6.87 (d, J=8.1 Hz, 1H), 6.85 (d, J=2.1 Hz, 1H), 6.78 (dd, J=8.3, 2.1 Hz, 1H), 4.98 (s, 2H), 4.53 (s, 2H), 4.47 (t, J=5.2 Hz, 1H), 4.35 (t, J=5.3 Hz, 1H), 3.44 (ddd, J=15.0, 10.2, 5.3 Hz, 1H), 3.33 (ddd, J=14.3, 10.5, 4.4 Hz, 1H), 2.72-2.58 (m, 2H), 2.12 (s, 3H), 2.07-1.99 (m, 2H), 1.88 (dq, J=12.7, 5.8 Hz, 1H), 1.82-1.67 (m, 3H), 1.51 (s, 6H), 1.41 (d, J=1.0 Hz, 9H).
$^{13}$C NMR (101 MHZ, Chloroform-d) δ 180.64, 148.64, 142.33, 139.74, 138.21, 135.64, 131.28, 124.32, 123.76, 122.39, 115.13, 83.97, 82.32, 80.90, 64.64, 55.54, 52.42, 52.32, 39.77, 29.88, 28.95, 28.81, 28.61, 26.75, 22.17, 18.84, 18.80. 19F NMR (376 MHz, Chloroform-d) 8-75.47 (s), −219.09 (tt, J=48.9, 26.0 Hz).

LC-MS (ESI): m/z [M+H]+calcd for $C_{29}H_{42}FN_2O_4S$ 533.2; found 533.2.

Example 16

The present embodiment provides a method for the preparation of compound 16, (2-(4-(3-(tert-butyl)-4-hydroxyphenyl)-2-methylbutan-2-yl)isoindol-5-yl)(iminyl)(methyl)-26-thiamine. Compound 1 (87 mg, 0.18 mmol), anhydrous potassium carbonate (0.1 g, 0.74 mmol) and methanol (5 ml) were added to a 50 ml single-necked vial and reacted under nitrogen protection at 75° C. for 1.5 h. After the reaction solution was cooled down to room temperature it was poured into water, extracted with ethyl acetate (15 ml×3), washed once with saturated brine (40 ml) and dried over anhydrous sodium sulfate. After evaporation, the trifluoroacetate of compound 16 was purified by pre-HPLC (C18 column, ACN: 0.1% TFA 10%~60% gradient elution) to obtain 31 mg, white solid, yield: 31.62%.

The structural formula of compound 16 is shown below:

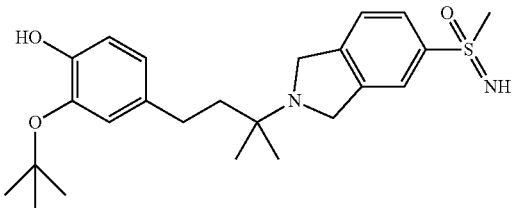 [SMILES: CC(C)(C)Oc1cc(CCC(C)(C)N2Cc3ccc(S(C)(=N)=O)cc3C2)ccc1O]

NMR and MS data for compound 16 are shown below:
$^1$H NMR (400 MHZ, Chloroform-d) δ 8.00 (d, J=8.2 Hz, 1H), 7.96 (s, 1H), 7.49 (d, J=8.1 Hz, 1H), 6.88 (d, J=8.1 Hz, 1H), 6.85 (d, J=2.0 Hz, 1H), 6.78 (dd, J=8.1, 2.0 Hz, 1H), 5.07 (s, 2H), 4.52 (s, 2H), 3.23 (s, 3H), 2.70-2.60 (m, 2H), 2.21-1.89 (m, 2H), 1.54 (s, 6H), 1.41 (d, J=0.9 Hz, 9H).
$^{13}$C NMR (101 MHZ, Chloroform-d) δ 148.56, 142.22, 139.53, 135.28, 131.13, 128.98, 123.66, 122.89, 122.24, 115.04, 80.89, 64.74, 52.31, 39.59, 29.83, 28.86, 22.13.
LC-MS (ESI): m/z [M+H]+calcd for $C_{24}H_{35}N_2O_3S$ 431.2; found 431.2.

Example 17

This embodiment provides a method for the preparation of compound 17, (2-(4-(3-(tert-butyl)-4-hydroxyphenyl)-2-methylbutan-2-yl)isoindol-5-yl)(ethyl)(iminyl)-26-thioimide, with reference to the method of preparing the compound of Example 16, which differs from Example 16 in that the trifluoroacetate of compound 17 was obtained by using compound 4 as a raw material, 145 mg white solid, yield: 63.15%.

The structural formula of compound 17 is shown below:

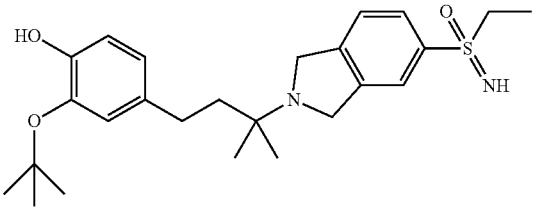

NMR and MS data for compound 17 are shown below:
$^1$H NMR (400 MHZ, Chloroform-d) δ 7.91 (d, J=8.9 Hz, 2H), 7.52 (d, J=8.0 Hz, 1H), 6.86 (d, J=4.3 Hz, 1H), 6.84 (d, J=2.9 Hz, 1H), 6.78 (dd, J=8.2, 2.0 Hz, 1H), 4.92 (s, 2H), 4.66 (s, 2H), 3.69 (dd, J=14.6, 7.4 Hz, 1H), 3.57 (dt, J=14.6, 7.2 Hz, 1H), 2.71-2.53 (m, 2H), 2.10-1.98 (m, 2H), 1.51 (s, 6H), 1.39 (s, 9H), 1.25 (t, J=7.3 Hz, 3H).
$^{13}$C NMR (101 MHZ, Chloroform-d) δ 148.60, 142.17, 141.31, 136.03, 131.16, 130.04, 124.39, 124.06, 123.75, 122.51, 115.11, 80.90, 65.02, 52.45, 52.31, 50.57, 39.71, 29.76, 28.79, 21.93, 6.76.
LC-MS (ESI): m/z [M+H]+calcd for $C_{25}H_{37}N_2O_3S$ 445.2; found 445.2.

Example 18

This embodiment provides a method for the preparation of compound 18, (2-(4-(3-(tert-butyl)-4-hydroxyphenyl)-2-methylbutan-2-yl)isoindol-5-yl)(iminyl)(propyl)-26-thiimide, with reference to the method of preparing the compound of Example 16, which differs from Example 16 in that trifluoroacetate of compound 18 was obtained by using compound 7 as a raw material 100 mg, white solid, yield: 51.36%.

The structural formula of compound 18 is shown below:

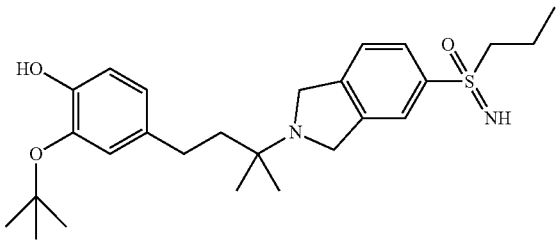 [SMILES: CCCS(=N)(=O)c1ccc2c(c1)CN(C(C)(C)CCc1ccc(O)c(OC(C)(C)C)c1)C2]

NMR and MS data for compound 18 are shown below:

$^1$H NMR (400 MHz, Chloroform-d) δ 7.92 (d, J=8.3 Hz, 1H), 7.89 (s, 1H), 7.46 (d, J=8.0 Hz, 1H), 6.86 (dd, J=8.1, 1.0 Hz, 2H), 6.78 (dd, J=8.2, 2.0 Hz, 1H), 4.79 (s, 4H), 3.33 (ddd, J=15.8, 10.8, 5.3 Hz, 1H), 3.29-3.16 (m, 1H), 2.72-2.56 (m, 2H), 2.08-1.96 (m, 2H), 1.85-1.69 (m, 1H), 1.68-1.57 (m, 1H), 1.52 (s, 6H), 1.40 (d, J=1.0 Hz, 9H), 0.96 (t, J=7.4 Hz, 3H).

$^{13}$C NMR (101 MHZ, Chloroform-d) δ 148.66, 142.30, 139.89, 135.49, 131.32, 129.67, 123.99, 123.79, 123.58, 122.53, 115.17, 80.94, 64.68, 58.49, 52.45, 52.33, 39.64, 29.90, 28.93, 22.16, 16.69, 12.60.

LC-MS (ESI): m/z [M+H]+calcd for $C_{26}H_{39}N_2O_3S$ 459.2; found 459.2.

Example 19

The present embodiment provides a method for the preparation of Compound 19, (2-(4-(3-(tert-butyl)-4-hydroxyphenyl)-2-methylbutan-2-yl)isoindol-5-yl)(butyl)(iminyl)-λ6-thiimide, with reference to the method of preparation of the compound of Example 16, which differs from Example 16 in that the trifluoroacetate salt of Compound 19 was synthesized using Compound 10 as the raw material to obtain 100 mg, white solid, yield: 67.37%.

The structural formula of compound 19 is shown below:

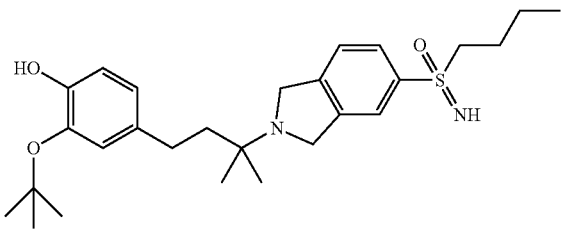 [SMILES: CCCCS(=N)(=O)c1ccc2c(c1)CN(C(C)(C)CCc1ccc(O)c(OC(C)(C)C)c1)C2]

NMR and MS data for compound 19 are shown below:

$^1$H NMR (400 MHZ, Chloroform-d) δ 7.94-7.84 (m, 2H), 7.50 (d, J=8.0 Hz, 1H), 6.83 (dd, J=5.2, 3.1 Hz, 2H), 6.76 (dd, J=8.2, 2.0 Hz, 1H), 4.92 (s, 2H), 4.61 (s, 2H), 3.76-3.63 (m, 1H), 3.58-3.45 (m, 1H), 2.71-2.53 (m, 2H), 2.09-1.94 (m, 2H), 1.75-1.60 (m, 1H), 1.49 (s, 7H), 1.37 (s, 9H), 1.35-1.25 (m, 2H), 0.83 (t, J=7.3 Hz, 3H).

$^{13}$C NMR (101 MHZ, Chloroform-d) δ 148.68, 142.27, 141.75, 136.27, 131.21, 124.61, 124.15, 123.83, 122.55, 115.20, 81.00, 65.20, 55.22, 52.56, 52.43, 39.85, 29.84, 28.88, 23.94, 22.01, 21.01, 13.17.

LC-MS (ESI): m/z [M+H]+calcd for $C_{27}H_{41}N_2O_3S$ 473.2; found 473.2.

Example 20

The present embodiment provides a method for the preparation of compound 20, (2-(4-(3-(tert-butyl)-4-hydroxyphenyl)-2-methylbutan-2-yl)isoindol-5-yl)(fluoromethyl)(iminyl)-26-thiimine. Referring to the method for the preparation of the compound of Example 16, unlike Example 16, 81 mg of the trifluoroacetate salt of Compound 20 was obtained by using Compound 13 as a raw material, white solid, yield: 65.44%.

The structural formula of compound 20 is shown below:

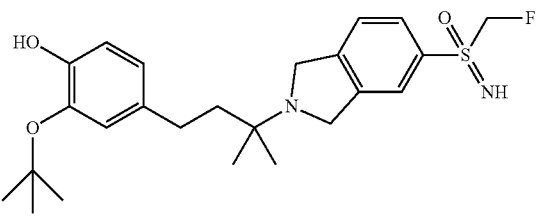 [SMILES: CC(C)(C)Oc1cc(CCC(C)(C)N2Cc3ccc(S(=N)(=O)CF)cc3C2)ccc1O]

NMR and MS data for compound 20 are shown below:

$^1$H NMR (400 MHZ, Chloroform-d) δ 7.98 (d, J=8.1 Hz, 1H), 7.92 (s, 1H), 7.48 (d, J=8.1 Hz, 1H), 6.86 (d, J=8.7 Hz, 1H), 6.85 (d, J=2.4 Hz, 1H), 6.77 (dd, J=8.4, 2.1 Hz, 1H), 5.24-4.96 (m, 5H), 4.55 (s, 1H), 2.68-2.58 (m, 2H), 2.08-1.97 (m, 2H), 1.52 (s, 6H), 1.40 (d, J=1.0 Hz, 9H).

$^{13}$C NMR (101 MHZ, Chloroform-d) δ 148.65, 142.33, 139.94, 139.12, 135.09, 131.19, 130.27, 124.11, 123.97, 123.74, 122.35, 115.14, 93.83, 91.61, 80.96, 65.05, 52.63, 52.46, 39.63, 29.88, 28.93, 22.21. 19F NMR (376 MHz, Chloroform-d) 8-75.57 (s), −203.62 (t, J=47.3 Hz).

LC-MS (ESI): m/z [M+H]+calcd for $C_{24}H_{34}FN_2O_3S$ 449.2; found 449.2.

Example 21

The present embodiment provides a method for the preparation of compound 21, (2-(4-(3-(tert-butyl)-4-hydroxyphenyl)-2-methylbutan-2-yl)isoindol-5-yl)(fluoropropyl)(iminyl)-16-thiimine. Referring to the method for the preparation of the compound of Example 16, unlike Example 16, the trifluoroacetate salt of Compound 21 was synthesized from Compound 14 as a raw material to obtain 126 mg of the trifluoroacetate salt of Compound 21 as a white solid, yield: 64.64%.

The structural formula of compound 21 is shown below:

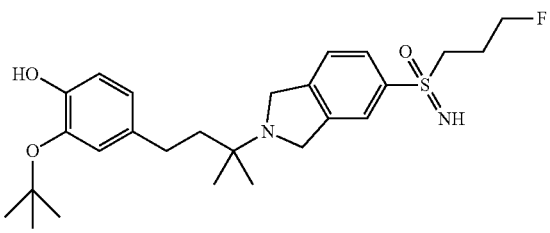 [SMILES: CC(C)(C)Oc1cc(CCC(C)(C)N2Cc3ccc(S(=N)(=O)CCCF)cc3C2)ccc1O]

NMR and MS data for compound 21 are shown below:

$^1$H NMR (400 MHZ, Chloroform-d) δ 7.91 (d, J=6.5 Hz, 2H), 7.51 (d, J=8.2 Hz, 1H), 6.85 (d, J=5.5 Hz, 1H), 6.84 (d, J=2.6 Hz, 1H), 6.78 (dd, J=8.2, 1.9 Hz, 1H), 4.95 (s, 2H), 4.61 (s, 2H), 4.49 (t, J=5.7 Hz, 1H), 4.37 (t, J=5.7 Hz, 1H), 3.73 (q, J=7.9, 5.0 Hz, 1H), 3.58 (td, J=10.1, 9.6, 5.3 Hz, 1H), 2.63 (dd, J=11.1, 6.0 Hz, 2H), 2.23-1.85 (m, 4H), 1.51 (s, 6H), 1.39 (s, 9H).

$^{13}$C NMR (101 MHZ, Chloroform-d) δ 148.69, 142.27, 141.11, 136.00, 131.23, 129.90, 124.50, 123.95, 123.83, 122.61, 115.21, 81.77, 81.01, 80.10, 65.12, 52.73, 52.55, 52.41, 39.82, 29.83, 28.87, 24.05, 23.84, 22.04. 19F NMR (376 MHz, Chloroform-d) 8-75.59 (s), −220.66 (tt, J=47.9, 25.8 Hz).

LC-MS (ESI): m/z [M+H]+calcd for $C_{26}H_{38}FN_2O_3S$ 477.2; found 477.2.

Example 22

This embodiment provides a method for the preparation of compound 22, (2-(4-(3-(tert-butyl)-4-hydroxyphenyl)-2-methylbutan-2-yl)isoindol-5-yl)(fluoro-butyl)(iminyl)-26-thiimine. Referring to the method for the preparation of the compound of Example 16, unlike Example 16, 100 mg of the trifluoroacetate salt of Compound 22 was obtained by using Compound 15 as a raw material, white solid, yield: 47.42%.

The structural formula of compound 22 is shown below:

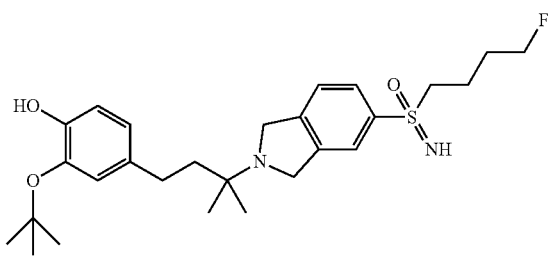 [SMILES: CC(C)(C)Oc1cc(CCC(C)(C)N2Cc3ccc(S(=N)(=O)CCCCF)cc3C2)ccc1O]

NMR and MS data for compound 22 are shown below:

$^1$H NMR (400 MHZ, Chloroform-d) δ 7.91 (d, J=8.8 Hz, 2H), 7.48 (d, J=8.0 Hz, 1H), 6.85 (dd, J=5.1, 3.2 Hz, 2H), 6.78 (dd, J=8.3, 2.0 Hz, 1H), 4.77 (s, 4H), 4.45 (t, J=5.2 Hz, 1H), 4.33 (t, J=5.2 Hz, 1H), 3.49 (d, J=8.3 Hz, 1H), 3.40 (td, J=10.2, 5.0 Hz, 1H), 2.69-2.57 (m, 2H), 2.10-1.97 (m, 2H), 1.91-1.80 (m, 1H), 1.80-1.64 (m, 3H), 1.51 (s, 6H), 1.39 (d, J=1.0 Hz, 9H).

$^{13}$C NMR (101 MHZ, Chloroform-d) δ 148.68, 142.30, 140.38, 135.74, 131.32, 129.74, 124.20, 123.81, 123.71, 122.60, 115.20, 83.96, 82.31, 80.94, 64.82, 56.14, 52.47, 52.36, 39.70, 29.87, 28.91, 28.68, 28.48, 22.10, 19.40, 19.36. 19F NMR (376 MHz, Chloroform-d) 8-75.45 (s), −219.17 (tt, J=47.6, 26.5 Hz).

LC-MS (ESI): m/z [M+H]+calcd for $C_{27}H_{40}FN_2O_3S$ 491.2; found 491.2 Embodiment The pharmacodynamic test methods employed in this embodiment are those known to those skilled in the art; the sigma-2 receptor inhibitory activity assay kit employed in this embodiment is commercially available to those skilled in the art. sigma1/sigma-2 receptor affinity activity test:

In a 96-well plate, eight 4-fold dilutions of the test and reference compounds were made, and 1 μL of each compound was added to each well, and the wells were rearranged. The reference compound Haloperidol was added at a starting concentration of 1 μM, 1 μL of DMSO was added to the high signal control wells (High control), and 1 μL of Haloperidol was added to the low signal control wells (Low control) at a concentration of 200 μM (final concentration of 1 μM), and 100 μL of desired concentration of sigma-1R or sigma-2R cell membrane, diluted in 50 mM Tris-HCl (pH 7.4, Sigma, Cat: T1503-1 KG) was added to each well and 100 μL of desired concentration of 3H-DTG diluted in 50 mM Tris-HCl (pH 7.4) was added to each well, the 96-well plate was sealed, and incubated for 2 hours at room temperature on a shaker at 300 rpm. Simultaneously, GF/C filter plates (PerkinElmer, Cat: NET986250UC) were soaked with 0.3% PEI (Poly ethyleneimine, Sigma, Cat: P3143). After incubation, the cells were collected onto GF/C filter plates with a cell collector (PerkinElmer, model: C961961), washed 4 times with 50 mM Tris-HCl (pH 7.4) wash buffer, and then dried in an oven at 50° C. for 1 h. The bottom of the dried GF/C filter plates were sealed with a membrane, and 50 μL of scintillation solution was added into each well and sealed, and the cells were read by using a Microbeta (PerkinElmer, model: 2450 Microplate Counter). The percentage of activity was calculated using Microsoft Excel software with the formula: % Activity=100×(Sample Raw-Value−High Control Average)/(Low Control Average-High Control Average), using GraphPad Prism 5 data analysis software. The Dose-response-Stimulation-log [antagonist] vs. response-Variable slope model was selected for fitting analysis to obtain the IC50 value of each tested sample, and the results are shown in Table 1. As can be seen from Table 1, the compounds of the present invention have good sigma-2 inhibitory activity and selectivity, and can be further developed for the treatment of sigma-2 receptor abnormality-related diseases, including but not limited to tumors, Alzheimer's disease, schizophrenia, dementia with Lewy bodies, and other diseases.

TABLE 1

Results of sigma1/sigma-2 receptor inhibition and affinity activity of compounds of the present invention.

| Compound | Sigma1 Binding Assay Summary | | Sigma 2 Binding Assay Summary | |
| --- | --- | --- | --- | --- |
| | IC$_{50}$ (nM) | Ki (nM) | IC$_{50}$ (nM) | Ki (nM) |
| 1 | >1000 | >1000 | >100 | >100 |
| 2 | >1000 | >1000 | >100 | >100 |
| 3 | >5000 | >5000 | >500 | >500 |
| 4 | >1000 | >1000 | >100 | >100 |
| 5 | >1000 | >1000 | >100 | >100 |
| 6 | >5000 | >5000 | >500 | >500 |
| 7 | >5000 | >5000 | >500 | >500 |
| 8 | >5000 | >5000 | >500 | >500 |
| 9 | >5000 | >5000 | >500 | >500 |
| 10 | >5000 | >5000 | >500 | >500 |
| 11 | >5000 | >5000 | >500 | >500 |
| 12 | >5000 | >5000 | >500 | >500 |
| 13 | >1000 | >1000 | >100 | >100 |
| 14 | >5000 | >5000 | >500 | >500 |
| 15 | >5000 | >5000 | >500 | >500 |
| 16 | >100 | >100 | <100 | <100 |
| 17 | >100 | >100 | <100 | <100 |
| 18 | >5000 | >5000 | >500 | >500 |
| 19 | >1000 | >1000 | >100 | >100 |
| 20 | >100 | >100 | <100 | <100 |
| 21 | >5000 | >5000 | >500 | >500 |
| 22 | >5000 | >5000 | >500 | >500 |

The isoindol-sulfilimine compounds prepared by the present invention are capable of acting as sigma-2 receptor inhibitors, including, but not limited to, for use in treating disorders associated with sigma-2 receptor overactivation, such as tumor formation and non-malignant overproliferation, and neurodegenerative disease nerve conduction disorders. Said diseases include ovarian cancer, pancreatic cancer, prostate cancer, lung cancer, breast cancer, renal cancer, hepatocellular carcinoma, cervical cancer, bone metastatic cancer, papillary thyroid cancer, colon cancer, gastrointestinal mesenchymal tumors, melanoma, mesothelioma, glioblastoma, osteosarcoma, multiple myeloma, hyperproliferative disorders, metastasis of primary tumor sites, myeloproliferative disorders, leukemias, metabolic diseases, neurodegenerative disease, schizophrenia, dementia, tachycardia, Parkinson's, rheumatic arthritis, rheumatoid arthritis, osteoarthritis, multiple sclerosis, autoimmune nephritis, lupus, Crohn's disease, asthma, chronic obstructive pulmonary disease (COPD), osteoporosis, hypereosinophilic syndrome, mast cell hyperplasia, or mast cell leukemia.

The foregoing description of embodiments is intended to facilitate the understanding and use of the invention by persons of ordinary skill in the art. A person skilled in the art can obviously easily make various modifications to these embodiments and apply the general principles illustrated herein to other embodiments without inventive steps. Therefore, the present invention is not limited to the above embodiments, and improvements and modifications made by persons skilled in the art in accordance with the disclosure of the present invention without departing from the scope of the present invention should be within the scope of protection of the present invention.

What is claimed is:

1. An isoindol-sulfilimine compound or a stereoisomer, solvate, or a pharmaceutically acceptable salt thereof, wherein said isoindol-sulfilimine compound has the chemical structural formula shown in formula (I):

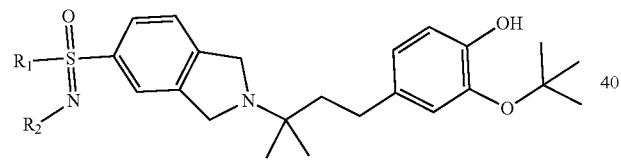

formula (I)

wherein $R_1$ is an alkyl group of 1-4 carbon atoms or an alkyl halide group of 1-4 carbon atoms; and $R_2$ is one of hydrogen, an alkyl group of 1-4 carbon atoms, an alkyl halide group of 1-4 carbon atoms and an acyl group of 1-4 carbon atoms.

2. An isoindol-sulfilimine compound according to claim 1, or a stereoisomer, solvate, or a pharmaceutically acceptable salt thereof, wherein said isoindol-sulfilimine compound is one of the following compounds 1-22:

8
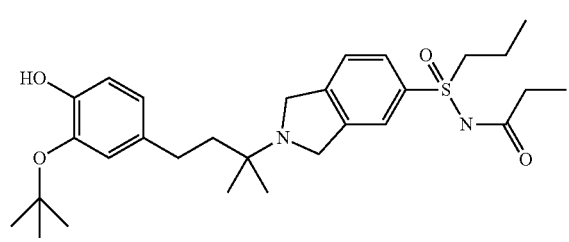
13
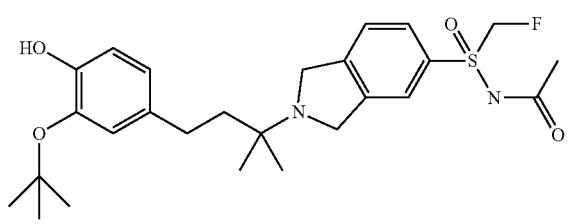
9
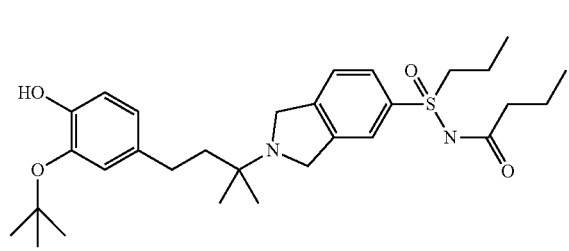
14
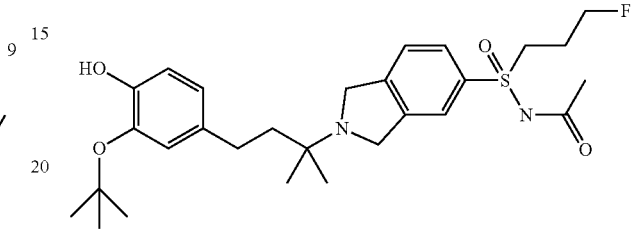
10
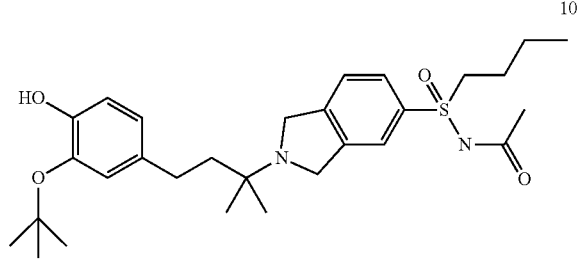
15
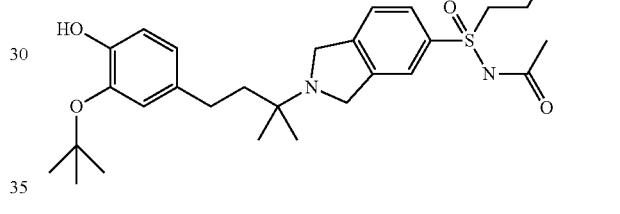
11
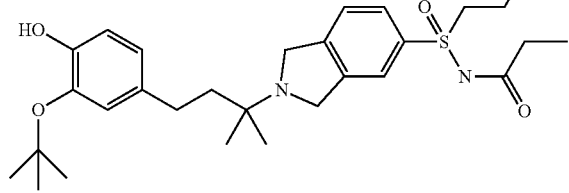
16
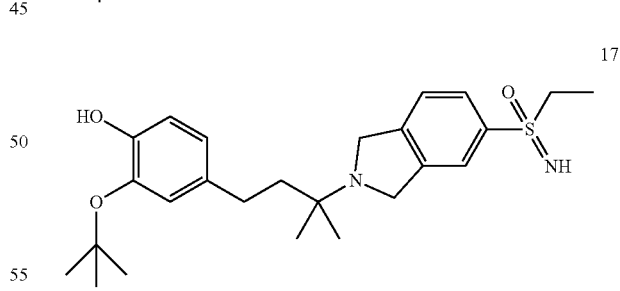
17
12
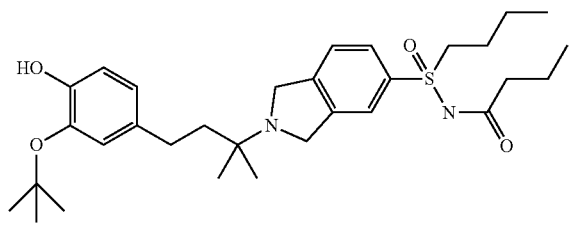
18
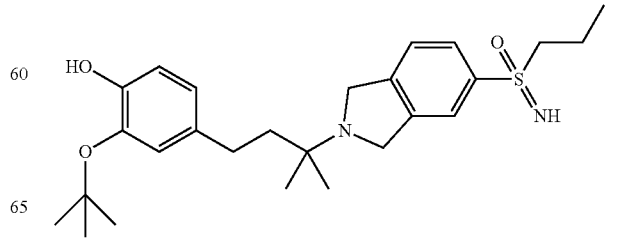

31
-continued
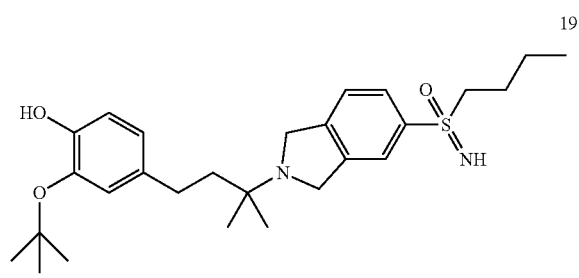
19
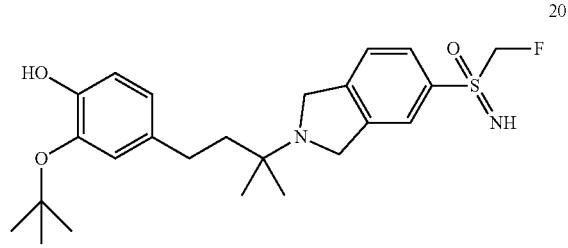
20
32
-continued
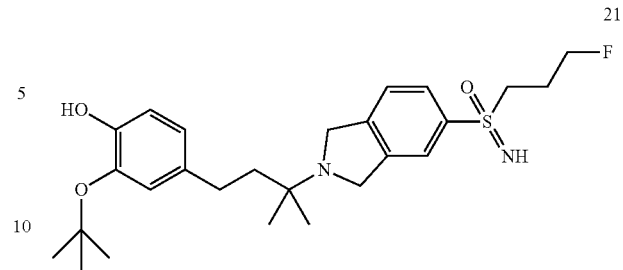
21
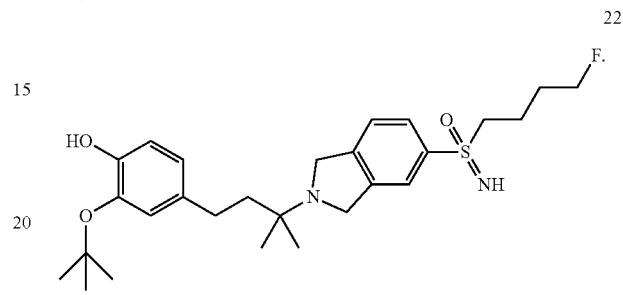
22
* * * * *